United States Patent [19]
Bartel et al.

[11] Patent Number: 5,811,433
[45] Date of Patent: Sep. 22, 1998

[54] 1,6-NAPHTHYRIDONECARBOXYLIC ACID DERIVATIVES

[75] Inventors: Stephan Bartel, Bergisch Gladbach; Klaus Grohe, Odenthal; Hermann Hagemann, Leverkusen; Klaus-Dieter Bremm, Recklinghausen; Rainer Endermann, Wuppertal, all of Germany

[73] Assignee: Bayer Aktiengesellschaft, Leverkusen, Germany

[21] Appl. No.: 878,683

[22] Filed: Jun. 19, 1997

Related U.S. Application Data

[63] Continuation of Ser. No. 595,603, Feb. 2, 1996, abandoned.

[30] Foreign Application Priority Data

Feb. 9, 1995 [DE] Germany ............... 195 04 280.8
Feb. 24, 1995 [DE] Germany ............... 195 06 535.2

[51] Int. Cl.$^6$ ............... C07D 471/02; A61K 31/435
[52] U.S. Cl. ............... 514/300; 546/123
[58] Field of Search ............... 546/123; 514/300

[56] References Cited

U.S. PATENT DOCUMENTS

| | | | |
|---|---|---|---|
| 3,637,716 | 1/1972 | Bimber et al. | 260/295 |
| 4,017,622 | 4/1977 | Minami et al. | 424/250 |
| 4,670,444 | 6/1987 | Grohe et al. | 514/300 |
| 5,464,796 | 11/1995 | Petersen et al. | 514/312 |

FOREIGN PATENT DOCUMENTS

| | | |
|---|---|---|
| 0588166 | 3/1994 | European Pat. Off. . |
| 0607825 | 7/1994 | European Pat. Off. . |
| 2656574 | 6/1978 | Germany . |
| 9519349 | 7/1995 | WIPO . |

OTHER PUBLICATIONS

P. Sanchez et al., J. Heterocyclic Chem., vol. 30, pp. 855–859 (1993).
P. Strehlke, Eur. J. Med. Chem., vol. 12, No. 6 pp. 541–547 (1977).
Chemical Abstracts, vol. 90, abstract No. 103851r, p. 583 abstract of USSR 638, 595 (1979).
Houben–Weyl, Methoden der Org. Chemie, vol. E4, p. 144 (1983).
J.F.W. McOmie, Protective Groups in Organic Chemistry (1973), p. 43.

*Primary Examiner*—Matthew V. Grumbling
*Attorney, Agent, or Firm*—Sprung Kramer Schaefer & Briscoe

[57] ABSTRACT

The invention relates to novel 1,6-naphthyridonecarboxylic acid derivatives, to processes for their preparation, to antibacterial compositions and feed additives in which they are present, and to novel intermediates for the preparation of these active compounds.

10 Claims, No Drawings

1,6-NAPHTHYRIDONECARBOXYLIC ACID DERIVATIVES

This application is a continuation of application Ser. No. 08/595,603, filed on Feb. 2, 1996, now abandoned.

The invention relates to novel 1,6-naphthyridonecarboxylic acid derivatives, to processes for their preparation, to antibacterial compositions and feed additives in which they are present, and to novel intermediates for the preparation of these active compounds.

It has already been disclosed that 1,6-naphthyridonecarboxylic acids of this kind are antibacterially active. Examples of this can be found in DE 3033157 A 1, DE 2626574, JP 50111096, JP 50111080, JP 50108294, JP 50108277, JP 50108276, JP 50076093, JP 50106974 and DE 2362553. 8-Fluoro-substituted 1,6-naphthyridones have been described in Journal of Heterocyclic Chemistry 30 (1993), 855.

Compounds of the general formula (I) have now been found

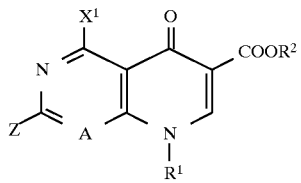

in which

R$^1$ represents straight-chain or branched C$_1$–C$_4$-alkyl which is optionally substituted by hydroxyl, halogen or C$_1$–C$_3$-alkoxy, or represents C$_3$–C$_6$-cycloalkyl which is optionally substituted by C$_1$–C$_3$-alkyl or halogen, or represents C$_2$–C$_4$-alkenyl, or furthermore represents C$_1$–C$_3$-alkoxy, amino, monoalkylamino having 1 to 3 carbon atoms, dialkylamino having 1 to 3 carbon atoms per alkyl group, or represents phenyl which is optionally substituted from one to three times by halogen, R$^2$ represents hydrogen, alkyl having 1 to 4 carbon atoms which is optionally substituted by hydroxyl, methoxy, amino, methylamino or dimethylamino, or represents (5-methyl-2-oxo-1,3-dioxol-4-yl)methyl, X$^1$ represents hydrogen, halogen, amino, methyl or trifluoromethyl, Z represents radicals of the structures

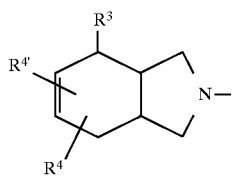

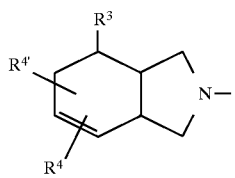

-continued

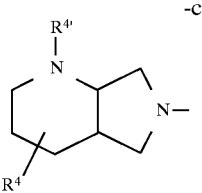

in which

R$^3$ represents hydrogen, hydroxyl, —NR$^5$R$^6$, hydroxymethyl or —CH$_2$—NR$^5$R$^6$, where R$^5$ denotes hydrogen, C$_1$–C$_3$-alkyl which is optionally substituted by hydroxyl, or denotes alkoxycarbonyl having 1 to 4 carbon atoms in the alkoxy moiety or denotes C$_1$–C$_3$-acyl, and R$^6$ denotes hydrogen or methyl, R$^4$ represents hydrogen, straight-chain or branched C$_1$–C$_3$-alkyl or cyclopropyl, R$^{4'}$ represents hydrogen or methyl, A represents C—R$^7$, in which R$^7$ represents hydrogen, halogen, methyl, tifluoromethyl, vinyl, ethinyl, hydroxyl or methoxy, or else, together with R$^1$, can form a bridge of the structure

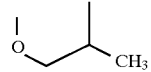

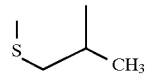

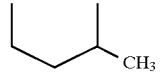

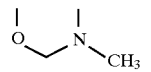

in the form of racemates or as enantiomerically pure compounds, pharmaceutically utilizable hydrates and acid addition salts thereof, and the alkali metal, alkaline earth metal, silver and guanidinium salts of the naphthyridonecarboxylic acids on which they are based. In comparison to known representatives of this structural type, the compounds according to the invention exhibit a higher antibacterial action, especially in the Gram-positive range.

They are therefore suitable as active compounds for human and veterinary medicine, in which context veterinary medicine includes the treatment of fish for purposes of therapy or to prevent bacterial infections.

Preferred compounds of the formula (I) are those in which

R$^1$ represents C$_1$–C$_2$-alkyl which is optionally substituted by hydroxyl or fluorine, or represents C$_3$–C$_5$-cycloalkyl which is optionally substituted by fluorine, or represents vinyl, amino, monoalkylamino having 1 to 2 carbon atoms, dialkylamino having 1 to 2 carbon atoms per alkyl group, or represents phenyl which is optionally substituted from one to two times by halogen, R$^2$ represents hydrogen, alkyl having 1 to 2 carbon atoms which is optionally substituted by amino or dimethylamino, or represents (5-methyl-2-oxo-1,3-dioxol-4-yl)-methyl, X$^1$ represents hydrogen, fluorine, chlorine, amino, methyl or trifluoromethyl, Z represents radicals of the structures

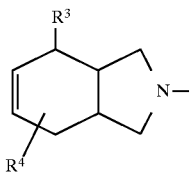

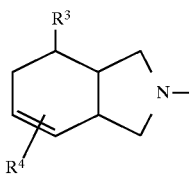

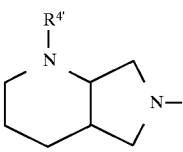

in which

R$^3$ represents hydrogen, hydroxyl, —NR$^5$R$^6$, hydroxymethyl or —CH$_2$—NR$^6$,
where
R$^5$ denotes hydrogen, C$_1$–C$_2$-alkyl which is optionally substituted by hydroxyl, or denotes alkoxycarbonyl having 1 to 4 carbon atoms in the alkoxy moiety, or denotes C$_1$–C$_3$-acyl, and
R$^6$ denotes hydrogen or methyl,
R$^4$ represents hydrogen, straight-chain or branched C$_1$–C$_3$-alkyl or cyclopropyl,
R$^{4'}$ represents hydrogen or methyl, A represents C—R$^7$, in which R$^7$ represents hydrogen, chlorine, fluorine, methyl, trifluoromethyl, hydroxyl or methoxy, or else, together with R$^1$, can form a bridge of the structure

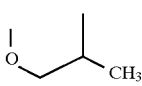

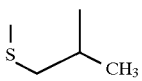

and the pharmaceutically utilizable hydrates and acid addition salts thereof, and also the alkali metal, alkaline earth metal, silver and guanidinium salts of the naphthyridonecarboxylic acids on which they are based Particularly preferred compounds of the formula (I) are those in which R$^1$ represents methyl, ethyl, cyclopropyl which is optionally substituted by fluorine, or represents phenyl which is optionally substituted from one to two times by fluorine,
R$^2$ represents hydrogen, methyl or ethyl,
X$^1$ represents hydrogen, methyl or trifluoromethyl, Z represents radicals of the structures

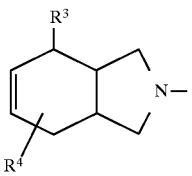

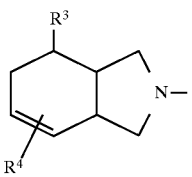

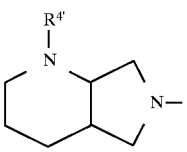

in which
R$^3$ represents hydrogen, hydroxyl, —NR$^5$R$^6$, hydroxymethyl or —CH$_2$—NR$^5$R$^6$,
where
R$^5$ denotes hydrogen, methyl, alkoxycarbonyl having 1 to 4 carbon atoms in the alkoxy moiety, or denotes C$_1$–C$_3$-acyl, and
R$^6$ denotes hydrogen or methyl,
R$^4$ represents hydrogen, straight-chain or branched C$_1$–C$_3$-alkyl or cyclopropyl,
R$^{4'}$ represents hydrogen or methyl,
A represents C—R$^7$ in Which
R$^7$ represents hydrogen, chlorine, fluorine or methoxy or else, together with R$^1$, can form a bridge of the structure

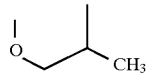

and the pharmaceutically utilizable hydrates and acid addition salts thereof, and also the alkali metal, alkaline earth metal, silver and guanidinium salts of the naphthyridonecarboxylic acids on which they are based.

It has additionally been found that compounds of the formula (I) are obtained if compounds of the formula (II)

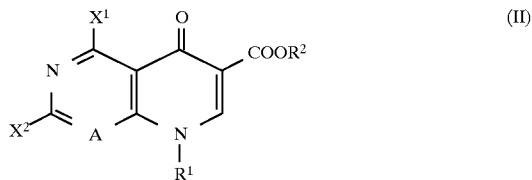

in which
R$^1$, R$^2$, X$^1$ and A are as defined above and
X$^2$ represents halogen, especially fluorine or chlorine, are reacted with compounds of the formula (III)

Z—H  (III)

in which
Z is as defined above, optionally in the presence of acid scavengers.

Using for example, 1-cyclopropyl-7,8-dichloro-1,4-dihydro-4-oxo-1,6-naphthyridine-3-carboxylic acid and 4-methylamino-1,3,3a,4,7,7a-hexahydroisoindole, the course of the reaction can be illustrated by the following equation:

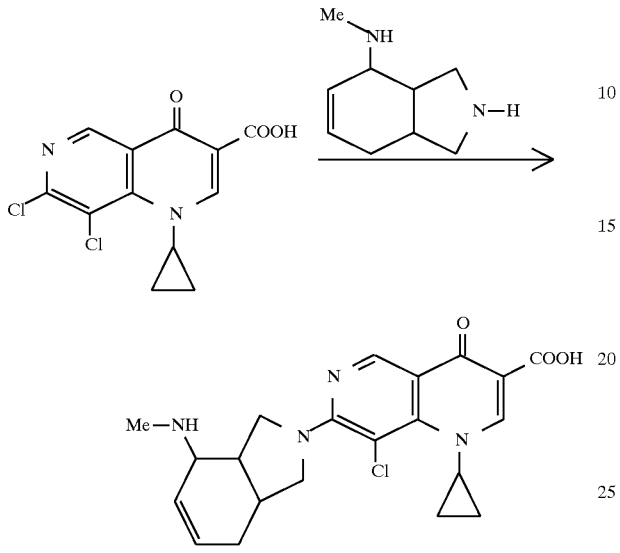

The compounds of the formula (II) used as starting compounds are in some cases known and in some cases novel. They can be employed if desired as racemates, pure enantiomers or diasteromers.

Examples of novel compounds of the formula (II) are those in which

R¹ represents methyl, ethyl, cyclopropyl Which is optionally substituted by fluorine, or represents phenyl which is optionally substituted from one to two times by fluorine, R² represents hydrogen, methyl or ethyl, X¹ represents hydrogen, methyl or trifluoromethyl, and X² represents halogen, preferably fluorine or chlorine, and A represents C—R⁷, in which R⁷ represents hydrogen, chlorine, fluorine or methoxy or else, together with R¹, can form a bridge of the structure

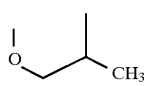

with the exception of compounds

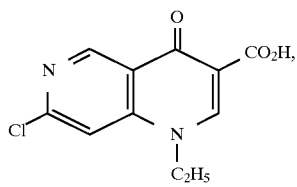

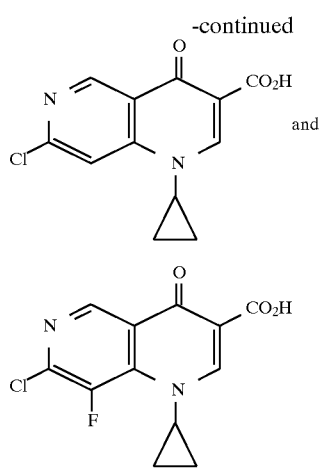

-continued and the methyl and ethyl esters thereof.

It has additionally been found that compounds of the formula (II) are obtained if compounds of the formula (IV)

in which X¹, X² and A are as defined above are reacted in a reaction sequence as described by way of example in preparative examples Ag. to Aj. The compounds of the formula (IV) used as starting compounds are, with the exception of the compound

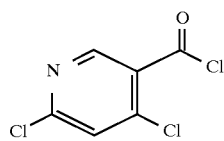

It has additionally been found that compounds of the formula (IV) in which X¹ represents hydrogen, X² represents chlorine and A represents CF and CCl are obtained if compounds of the formula (V)

in which X represents chlorine or fluorine are reacted in a reaction sequence as described by way of example in preparative enables Aa. to Af.

It has additionally been found that a compound of the formula (IVa) is obtained

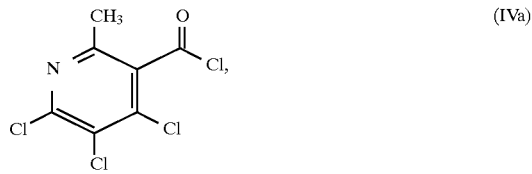

if trichloroacryloyl chloride is reached in a reaction sequence as described in Examples Ia. to Id.

The starting compounds for the reaction sequences Ag. to Aj. and Ia. to Id. are, apart from 3,3-dichloro-2- fluoroacryloyl chloride, known. 3,3-Dichloro-2-fluoroacryloyl chloride can be prepared by partial hydrolysis from the known 2-fluoro-1,1,3,3,3-pentachloropropene and is the subject of DE-A 4 401 099.

The amines of the formula (III) used as starting compounds have been described in EP 520 240 and EP 588 166. Chiral amines can be employed either as racemates or as enantiomerically or diastereomerically pure compounds.

The reaction of (II) with (III), in which the compounds (III) may also be employed in the form of their salts, for example the hydrochlorides, is preferably carried out in a diluent such as dimethyl sulphoxide, N,N-diethylformamide, N-methylpyrrolidone, hexamethylphosphoric triamide, sulpholane, acetonitrile, water, an alcohol such as methanol, ethanol, n-propanol, isopropanol or glycol monomethyl ether, or pyridine. It is also possible to use mixtures of these compounds.

As acid-binding agents it is possible to use all customary inorganic and organic acid-binding agents. These include, preferably, the alkai metal hydroxides, alkali metal carbonates, organic amines and amidines. Specific compounds which are particularly suitable are: triethylamine, 1,4-diazabicyclo[2.2.2]octane (DABCO), 1,8-diazabicyclo[5.4.0]undec-7-ene (DBU) or excess amine (III).

The reaction temperatures can be varied within a wide range. The reaction is generally carried out between about 0° and 200° C., preferably between 20° and 140° C.

The reaction can be carried out at atmospheric pressure or else at elevated pressure. In general it is carried out at pressures of between about 1 and 100 bar, preferably between 1 and 10 bar.

In carrying out the process according to the invention, from 1 to 15 mol, preferably from 1 to 6 mol, of the compound (III) are employed per mole of the compound (II).

Free amino groups can be protected during the reaction by a suitable amino-protective group, for example by the tert-butoxycarbonyl radical, and after the end of the reaction can be liberated by treatment with a suitable acid, such as hydrochloric acid or trifluoroacetic acid (see Houben-Weyl, Methoden der Organischen Chemie, Volume E4, page 144 (1983); J. F. W. McOmie, Protective Groups in Organic Chemistry (1973), page 43).

The esters according to the invention are obtained by reacting an alkali metal salt of the carboxylic acid on which they are based which may if desired be protected at the nitrogen atom by a protective group such as the tert-butoxycarbonyl radical, with suitable halogenoalkyl derivatives in a solvent such as dimethylformamide, dimethylacetamide, N-methylpyrrolidone, dimethyl sulphoxide or tetramethylurea, at temperatures of about 0°–100° C., preferably from 0° to 50° C.

The acid addition salts of the compounds according to the invention are prepared in conventional manner, for example by dissolving the betaine in a sufficient amount of aqueous acid and precipitating the salt with a water-miscible organic solvent such as methanol, ethanol, acetone or acetonitrile. It is also possible to heat equivalent amounts of betaine and acid in water or in an alcohol such as glycol monomethyl ether, and then to evaporate the mixture to dryness or to filter off the precipitated salt with suction. Examples of pharmaceutically utilizable salts are the salts of hydrochloric acid, sulphuric acid, acetic acid, glycolic acid, lactic acid, succinic acid, citric acid, tartaric acid, methanesulphonic acid, 4toluenesulphonic acid, galacturonic acid, gluconic acid, embonic acid, glutamic acid or aspartic acid.

The alkali metal salts or alkaline earth metal salts of the compounds according to the invention are obtained, for example, by dissolving the betaine in less than the equivalent amount of alkali metal hydroxide or alkaline earth metal hydroxide solution, filtering to remove undissolved betaine, and evaporating the filtrate to dryness. Pharmaceutically suitable salts are those of sodium, potassium or calcium. By reaction of an alkali metal salt or alkaline earth metal salt with an appropriate silver salt such as silver nitrate, the corresponding silver salts are obtained.

The compounds according to the invention have a strong antibiotic action and, despite being of low toxicity, display a broad antibacterial spectrum with respect to Gram-positive and Gram-negative microorganisms, including in particular those which are resistant to various antibiotics, for example penicillins, cephalosporins, aminoglycosides, sulphonamides, tetracyclines and to commercially available quinolones.

These valuable properties allow them to be used as chemotherapeutic active compounds in medicine and as preservatives for inorganic and organic materials, for example polymers, lubricants, paints, fibres, leather, paper and wood, foodstuff and water.

The compounds according to the invention are active against a very broad spectrum of microorganisms. Using these compounds it is possible to combat Gram-negative and Gram-positive bacteria and bacteria-like microorganisms and to prevent, alleviate and/or cure the diseases caused by these pathogens.

The compounds according to the invention are distinguished by an intensified action on dormant microorganisms. In the case of dormant bacteria, i.e. bacteria which show no detectable growth, the compounds have a strong bactericidal action. This applies not only to the amount to be employed, but also to the speed of destruction. Such results have been observed in the case of Gram-positive and Gram-negative bacteria, in particular for *Staphylococcus aureus, Pseudomonas aeruginosa, Enterococcus faecalis* and *Escherichia coli.*

The compounds according to the invention are particularly active against typical and atypical mycobacteria and *Helicobacter pylori* and against bacteria-like microorganisms, such as, for example, mycoplasms and rickettsias. They are therefore particularly suitable in human and veterinary medicine for the prophylaxis and chemotherapy of local and systemic infections which are caused by these pathogens.

In addition, the compounds are also particularly suitable for the control of protozoonoses and helminthoses.

The compounds according to the invention can be used in a variety of pharmaceutical preparations. Preferred pharmaceutical preparations which may be mentioned are plain and coated tablets, capsules, pills, granules, suppositories, solutions, suspensions and emulsions, pastes, ointments, gels, creams, lotions, powders and sprays.

The compounds according to the invention can be also be linked with β-lactam derivatives such as, for example, cephalosporins or penemens via covalent bonds to form so-called dual-action derivatives.

The minimum inhibitory concentrations (MIC) were determined by a serial dilution method on Iso-Sensitest Agar (Oxoid). For each test substance, a series of agar plates was prepared which contained concentrations of the active compound which decrease at a rate of in each case twice the dilution factor. The agar plates were inoculated using a multipoint inoculator (Denley). For inoculation, overnight cultures of the pathogens were used which had been diluted beforehand in such a manner that each inoculation point contained about $10^4$ colony-forming particles. The inoculated agar plates were incubated at 37° C. and the microbial growth was read off after about 20 hours. The MIC value (μg/ml) indicates the lowest concentration of active compound at which no growth can be detected by the naked eye.

The MIC values of some of the compounds according to the invention are listed in the table below in comparison with 7-(3-aminopyrrolidin-1-yl)-1-cyclopropyl-8-fluoro-1,4-dihydro-4-oxo-1,6-naphthyridine-3-carboxylic acid (Journal of Heterocyclic Chemistry 30 (1993), 855) as reference compound.

TABLE 1

| Example | | 6 | 33 | 43 | 49 | Reference |
|---|---|---|---|---|---|---|
| E. Coli | Neumann | 0.015 | 0.062 | 0.015 | 0.015 | 0.25 |
| | ATCC 25922 | 0.062 | 0.125 | 0.031 | 0.015 | 0.25 |
| Klebsiella | 8085 | 0.125 | 0.25 | 0.062 | 0.031 | 0.5 |
| | 63 | 0.125 | 0.25 | 0.062 | 0.031 | 0.5 |
| Enterobacter | cloaceac 2427 | 0.25 | 0.25 | 0.125 | 0.062 | 0.5 |
| | aerog.5240 | 16 | 16 | 8 | 2 | 32 |
| Morganella | morg.932 | 0.125 | 0.125 | 0.125 | 0.031 | 0.5 |
| Providencia | 12012 | 0.125 | 0.25 | 0.062 | 0.062 | 0.5 |
| | 12052 | 4 | 8 | 2 | 1 | 64 |
| Micrococ. | luteus 9341 | 0.25 | 0.125 | 0.062 | 2 | 8 |
| Staph. aureus | ICB 25701 | 0.125 | 1 | 0.062 | 1 | 128 |
| | ATCC 29213 | 0.015 | 0.031 | 0.015 | 0.031 | 2 |
| | I33 | 0.015 | 0.031 | 0.015 | 0.031 | 2 |
| Enterococcus | 27101 | 0.125 | 0.125 | 0.062 | 0.5 | 4 |
| | 9790 | 0.125 | 0.125 | 0.062 | 0.5 | 4 |
| Acinetobacter | 14068 | 0.06 | 0.5 | 0.015 | 0.031 | 4 |
| Staph. aureus | ICB 25768 | 0.25 | 2 | 0.125 | 8 | 128 |

PREPARATION OF THE INTERMEDIATES

EXAMPLE A 7,8-Dichloro-1-cyclopropyl-1,4-dihydro-4-oxo-1,6-naphthyridine-3-carboxylic acid

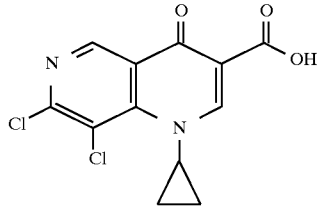

a. Ethyl 4,5,5-trichloro-3-oxo-4-pentenoate 16.9 g (0.695 mol) of magnesium turnings are placed in 35 ml of ethanol and the reaction is started with 3.5 ml of tetrachloromethane. Subsequently, a mixture of 112 g (0.7 mol) of diethyl malonate, 280 ml of toluene and 75 ml of ethanol is added dropwise such that the temperature is 50°–60° C. The mixture is then stirred at this temperature for one hour. After cooling to −10° to −5° C., a solution of 135.8 g (0.7 mol) of trichloroacryloyl chloride in 70 ml of toluene is added dropwise, and the mixture is stirred at 0° C. for one hour and then, while warming to room temperature, overnight.

The mixture is added to ice-water, 35 ml of concentrated sulphuric acid are added, and the phases are separated. The aqueous phase is extracted with toluene, and the combined organic phases are washed with saturated sodium chloride solution, dried over sodium sulphate and concentrated on a rotary evaporator.

The residue is heated at reflux in 370 ml of water with 1.1 g of p-toluenesulphonic acid for four hours. It is extracted with dichloromethane, washed with saturated sodium chloride solution and dried over sodium sulphate and the solvent is remove in vacuo.

Yield: 160 g (93% of theory)
Boiling point: 134°–136° C. (15 mbar)

b. Ethyl 4,5,5-trichloro-2-ethoxymethylene-3-oxo-4-pentenoate 305 g (1.24 mol) of ethyl 4,5,5-trichloro-3-oxo-4-pentenecarboxylate are heated with 275 g (1.86 mol) of ethyl orthoformate and 316.0 g of acetic anhydride at 150°–160° C. for three hours. All volatile components are removed initially in vacuo, then under a high vacuum up to 100° C.

Yield: 312.0 g (83% of theory)

c. Ethyl 2-aminomethylene-4,5,5-trichloro-3-oxo-4-pentenoate 180.6 g (0.6 mol) of ethyl 4,5,5-trichloro-2-ethoxy-3-oxo-4-pentenoate are placed in 600 ml of ethanol, and 90 ml of concentrated aqueous ammonia solution (25%) are added dropwise with ice cooling at a rate such that the temperature does not exceed 10° C.

1.2 l of water are added to the mixture, the mixture is cooled in an ice bath, and the product which crystallizes out is isolated. The precipitate is washed with ethanol/water 1:2.

Yield: 143.1 g (87% of theory)
Melting point: 105°–106° C.

d. Ethyl 5,6-dichloro-4-hydroxy-nicotinate 131 g (0.48 mol) of ethyl 2-aminomethylene-4,5,5-trichloro-3-oxo-4-pentenoate are heated in 1,2-dichlorobenzene at 180° C. for three hours. The volatile components are removed in vacuo up to 90° C. and then under a high vacuum up to 80° C.

Yield: 116.5 g (crude product)
Melting point: 92°–94° C. (from cyclohexane)

e. 5,6Dichloro-4-hydroxy-nicotinic acid 114 g (0.483 mol) of ethyl 5,6-dichloro-4-hydroxy-nicotinate are boiled under reflux in 1200 ml of water with 58 g (1.03 mol) of potassium hydroxide for two hours. The cooled mixture is stirred with activated charcoal and filtered, and the filtrate is brought to a pH of 1 with half-concentrated hydrochloric acid, while cooling with ice. The product which precipitates is isolated, washed with water and dried.

Yield: 84.2 g (83% of theory)
Melting point: 208°–210° C. (with decomposition)

f. 4,5,6-Trichloronicotinoyl chloride 84 g (0.404 mol) of 5,6-dichloro-4-hydroxynicotinic acid are heated slowly at reflux with 380 ml of phosphorus oxychloride and one drop of DMF. After two hours, the phosphorus oxychloride is distilled off in vacuo at about 100° C. The residue is put into ice-water and extracted with chloroform, and the extract is dried over sodium sulphate and concentrated on a rotary evaporator.

The residue is heated at reflux in 200 ml of thionyl chloride for thirty minutes, the thionyl chloride is distilled off in vacuo, and the residue is distilled directly under a high vacuum Yield: 78.8 g (79% of theory)
Boiling point: 96°–98° C. (0.14 mbar)
Melting point: 41°–42° C.

g. Ethyl 2-(4,5,6-trichloronicotinoyl)acetate 16.9 g (0.7 mol) of magnesium turnings are placed in 35 ml of ethanol, and the reaction is started with 3.5 ml of tetrachloromethane. Subsequently, a mixture of 112 g (0.7 mol) of diethyl malonate, 280 ml of toluene and 75 ml of ethanol is added dropwise at a rate such that the temperature is between 50° and 60° C. The mixture is then stirred for a further hour at this temperature.

At from −10° to −5° C., a solution of 171.5 g (0.7 mol) of 4,5,6-trichloronicotinoyl chloride in 70 ml of toluene is added dropwise, and the mixture is stirred at 0° C. for one hour and then, while warming to room temperature, overnight.

Ice-water is added to the mixture, and 35 ml of concentrated sulphuric acid are added dropwise. The phases are separated and the aqueous phase is again extracted with dichloromethane. The combined organic phases are washed with saturated sodium chloride solution, dried over sodium sulphate and concentrated on a rotary evaporator.

The residue is boiled under reflux with 1.1 g of para-toluenesulphonic acid in 350 ml of water for four hours. The cooled mixture is extracted with dichloromethane, the organic phases are dried over sodium sulphate, and the solvent is removed in vacuo.

Yield: 116.5 g (56% of theory)

Melting point: 79°–80° C.

h. Ethyl 2-(4,5,6-trichloronicotinoyl)-3-ethoxy-acrylate 87.0 g (0.29 mol) of ethyl 2-(4,5,6-trichloronicotinoyl) acetate are heated with 56.2 g of (0.38 mol) of ethyl orthoformate and 65.2 g of acetic anhydride at 150°–160° C. for two hours. All volatile components are removed, initially in vacuo and then under a high vacuum up to 100° C.

Yield: 93 g (90% of theory)

i. Ethyl 2-(4,5,6-trichloronicotinoyl-3-cyclopropylamino-acrylate 22.3 g (0.063 mol) of ethyl 2-(4,5,6-trichloronicotinoyl) -3-ethoxyacrylate are placed at 0° C. in 95 ml of ethanol, and 3.6 g (0.063 mol) of cyclopropylamine are added dropwise. The mixture is stirred at room temperature for two hours, 95 ml of water are added, it is cooled to 0° C., and the product which precipitates is isolated.

Yield: 17.5 g (76% of theory)

Melting point: 126°–128° C.

j. Ethyl 7,8-dichloro-1-cyclopropyl-1,4-dihydro-4-oxo-1,6-naphthyridine-3-carboxylate 17.5 g (0.048 mol) of ethyl 2-(4,5,6-trichloronicotinoyl) -3-cyclopropylamino-acrylate are heated with 7.7 g (0.056 mol) of potassium carbonate in 100 ml of DMF at 60° C. for two hours. Ice-water is added to the cooled mixture, and the product is isolated.

Yield: 15 g (95% of theory)

Melting point: 197°–199° C.

k. 7,8Dichloro-1-cyclopropyl-1,4-dihydro-4-oxo-1,6-naphthyridine-3-carboxylic acid 14.6 g (0.045 mol) of ethyl 7,8-dichloro-1-cyclopropyl-1,4-dihydro-4-oxo-1,6-naphthyridine-3-carboxylate are heated at reflux in a mixture of 59 ml of acetic acid, 59 ml of water and 5.9 ml of concentrated sulphuric acid for two hours. The cooled mixture is put into ice-water, and the product is isolated and washed with water.

Yield: 12.5 g (92% of theory)

Melting point: 215°–217° C.

EXAMPLE B 7,8-Dichloro-1-(2,4-difluorophenyl)-1,4-dihydro-4-oxo-1,6-naphthyridine-3-carboxylic acid

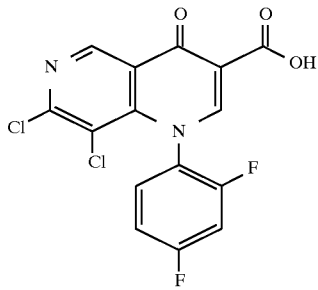

a. Ethyl 2-(4,5,6-trichloronicotinoyl)-3-(2,4-difluorophenyl) amino-acrylate 10.57 g (0.03 mol) of ethyl 2(4,5,6-trichloronicotinoyl)-3-ethoxyacrylate are placed at 0° C. in 45 ml of ethanol, and 4.2 g (0.033 mol) of 2,4-difluoroaniline are added dropwise. The mixture is stirred at room temperature for two hours, 45 ml of water are added, it is cooled to 0° C. and the product which precipitates is isolated.

Yield: 11.0 g (84% of theory)

Melting point: 128°–130° C.

b. Ethyl 7,8-dichloro-1-(2,4-difluorophenyl)-1,4-dihydro-4-oxo-1,6-naphthyridine-3-carboxylate 10.5 g (0.024 mol) of ethyl 2-(4,5,6-trichloronicotinoyl-3-(2,4-difluorophenyl)amino-acrylate are stirred with 4.8 g (0.028 mol) of potassium carbonate in 50 ml of DMF at room temperature overnight. Ice-water is added to the mixture, and the product is isolated.

Yield: 8.7 g (90% of theory)

Melting point: 199°–201° C.

c. 7,8-Dichloro-1-(2,4-difluorophenyl)-1,4-dihydro-4-oxo-1,6-naphthyridine-3-carboxylic acid 8.6 g (0.022 mol) of ethyl 7,8-dichloro-1-(2,4-difluorophenyl)-1,4-dihydro-4-oxo-1,6-naphthyridine-3-carboxylate are heated at reflux in a mixture of 29 ml of acetic acid, 29 ml of water and 2.9 ml of concentrated sulphuric acid for two hours. The cooled mixture is put into ice-water, and the product is isolated and washed with water.

Yield: 7.2 g (88% of theory)

Melting point: 206°–208° C.

EXAMPLE C 7,8-Dichloro-1-ethyl-1,4-dihydro-4-oxo-1,6-naphthyridine-3-carboxylic acid

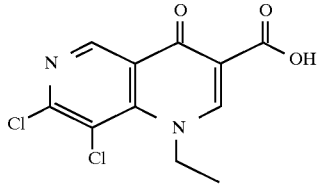

a. Ethyl 2-(4,5,-trichloronicotinoyl)-3-ethylamino-acrylate 10.57 g (0.03 mol) of ethyl 2-(4,5,6-trichloronicotinoyl) -3-ethoxyacrylate are placed at 0° C. in 45 ml of ethanol, and 2.21 ml (0.033 mol) of ethylamine solution (70%) are added dropwise. The mixture is stirred at room temperature for two hours, 45 ml of water are added, it is cooled to 0° C., and the product which precipitates is isolated.

Yield: 7.9 g (75% of theory)
Melting point: 133°–135° C.

b. Ethyl 7,8-dichloro-1-ethyl-1,4-dihydro-4-oxo-1,6-naphthyridine-3-carboxylate 7.5 g (0.024 mol) of ethyl 2-(4,5,-trichloronicotinoyl)-3-ethylamino-acrylate are stirred with 3.37 g (0.0244 mol) of potassium carbonate in 50 ml of DMF at room temperature overnight. Ice-water is added to the mixture and the product is isolated.

Yield: 6.4 g (84% of theory)
Melting point: 127°–128° C.

c. 7,8-Dichloro-1-ethyl-1,4-dihydro-1,6-naphthyridine-3-carboxylic acid 6.2 g (0.0196 mol) of ethyl 7,8-dichloro-1-ethyl-1,4-dihydro-4-oxo-1,6-naphthyridine-3-carboxylate are heated at reflux in a mixture of 26 ml of acetic acid, 26 ml of water and 2.6 ml of concentrated sulphuric acid for two hours. The cooled mixture is put into ice-water, and the product is isolated and washed with water.

Yield: 5.5 g (98% of theory)
Melting point: 219°–220° C.

EXAMPLE D 7,8-Dichloro-1-(4-fluorophenyl)-1,4-dihydro-4-oxo-1,6-naphthyridine-3-carboxylic acid

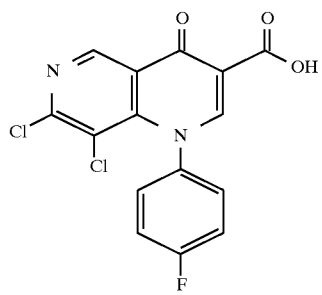

a. Ethyl 2-(4,5,6-trichloronicotinoyl)-3-(4-fluorophenyl)amino-acrylate 5.0 g, (0.014 mol) of ethyl 2-(4,5,6-trichloronicotinoyl)-3-ethoxyacrylate are placed at 0° C. in 21 ml of ethanol, and 1.7 g (0.0154 mol) of 4-fluoroaniline are added dropwise. The mixture is stirred at room temperature for two hours, 45 ml of water are added, it is cooled to 0° C., and the product which precipitates is isolated. The crude product is washed with water/ethanol 1:1.

Yield: 4.9 g (83% of theory)
Melting point: 126°–127° C.

b. Ethyl 7,8-dichloro-1-(4-fluorophenyl)-14-dihydro-4-oxo-1,6-naphthyridine-3-carboxylate 4.8 g (0.012 mol) of ethyl 2-(4,5,6-trichloronicotinoyl)-3-(4-fluorophenyl)amino-acrylate are stirred with 1.9 g (0.0138 mol) of potassium carbonate in 24 ml of DMF at room temperature overnight. Ice-water is added to the mixture and the product is isolated. The crude product is stirred up with acetonitrile.

Yield: 3.36 g (78% of theory)
Melting point: 219°–224° C.

c. 7,8Dichloro-1-(4-fluorophenyl)-1,4-dihydro-4-oxo-1,6-naphthyridine-3-carboxylic acid 3.3 g (0.0087 mol) of ethyl 7,8-dichloro-1-(4-fluorophenyl)-1,4-dihydro-4-oxo-1,6-naphthyridine-3-carboxylate are heated at reflux in a mixture of 11.5 ml of acetic acid, 11.5 ml of water and 1.15 ml of concentrated sulphuric acid for two hours. The cooled mixture is put into ice-water, the product is isolated and washed with water.

Yield: 2.9 g (94% of theory)
Melting point: 274°–276° C.

EXAMPLE E 7,8-Dichloro-1-(2-fluoroethyl)-1,4-dihydro-4-oxo-1,6-naphthyridine-3-carboxylic acid

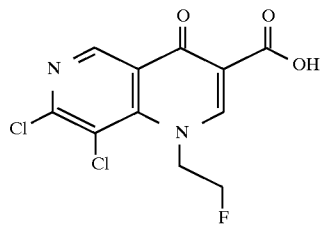

a. Ethyl 2-(4,5,6-trichloronicotinoyl)-3-(2-fluoroethyl)amino-acrylate 5.0 g (0.0142 mol) of ethyl 2-(4,5,6-trichloronicotinoyl)-3-ethoxyacrylate and 1.4 g (0.0142 mol) of fluoroethylamino hydrochloride are placed at 0° C. in a mixture of 22 ml of dichloromethane and 8.5 ml of water, and a solution of 1.2 g of sodium hydrogen carbonate in 14 ml of water is added dropwise. The mixture is stirred at room temperature for three hours, the phases are separated, and the organic phase is dried over sodium sulphate and concentrated on a rotary evaporator.

Yield: 5.7 g of crude product b. Ethyl 7,8-dichloro-1-(2-fluoroethyl-1,4-dihydro-4-oxo-1,6-naphthyridine-3-carboxylate 5.5 g (0.0148 mol) of ethyl 2-(4,5,6-trichloronicotinoyl)-3-(2-fluoroethyl)amino-acrylate are stirred with 2.4 g (0.0174 mol) of potassium carbonate in 30 ml of DMF at room temperature overnight. Ice-water is added to the mixture and the product is isolated.

Yield: 3.5 g (71% of theory)
Melting point: 168°–169° C.

c. 7,8-Dichloro-1-(2-fluoroethyl)-1,4-dihydro-4-oxo-1,6-naphthyridine-3-carboxylic acid 3.33 g (0.01 mol) of ethyl 7,8-dichloro-1-(2-fluoroethyl)-1,4-dihydro-4-oxo- 1,6-naphthyridine-3-carboxylate are heated at reflux in a mixture of 13 ml of acetic acid, 13 ml of water and 1.3 ml of concentrated sulphuric acid for two hours. The cooled mixture is put into ice-water, and the product is isolated and washed with water.

Yield: 2.7 g (88% of theory)
Melting point: 226°–228° C.

EXAMPLE F 7,8-Dichloro-1-[(1R,2S)-2-fluorocyclopropyl]-1,4-dihydro-4-oxo-1,6-naphthyridine-3-carboxylic acid

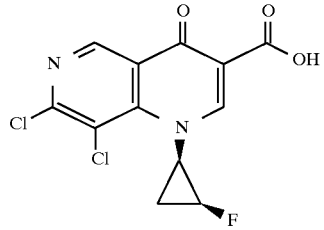

a. Ethyl 2-4,5,6trichloronicotinoyl)-3-[(1R,2S)-2-fluorocyclopropyl]aminoacrylate 6.35 g (0.018 mol) of ethyl 2-(4,5,6-trichloronicotinoyl)-3-ethoxyacrylate and 2.0 g (0.018 mol) of (1R,2S)-2- fluorocyclopropylamine hydrochloride are placed at 0° C. in a mixture of 27 ml of dichloromethane and 10.8 ml of water, and a solution of 1.5 g of sodium hydrogen carbonate in 18 ml of water is added dropwise. The mixture is stirred at room temperature for four hours, the phases are separated, and the organic phase is dried over sodium sulphate and concentrated on a rotary evaporator.

Yield: 6.6 g of crude product b. Ethyl 7,8-dichloro-1[(1R,2S)-2-fluorocyclopropyl]-1,4-dihydro-4-oxo-1,6-naphthyridine-3-carboxylate 6.6 g (0.017 mol) of ethyl 2-(4,5,6-trichloronicotinoyl)-3-[(1R,2S)-2-fluorocyclopropyl]aminoacrylate are stirred with 2.7 g (0.019 mol) of potassium carbonate in 35 ml of DMF at room temperature overnight. Ice-water is added to the mixture and the product is isolated.

Yield: 4.6 g (78% of theory)
Melting point: 198°–200° C.

c. 7,8-Dichloro-1-[(1R,2S)-2-fluorocyclopropyl]-1,4-oxo-1,6-naphthyridine-3-carboxylic acid 4.4 g (0.0128 mol) of ethyl 7,8-dichloro-1-[(1R,2S)-2-fluorocyclopropyl]-1,4-dihydro-4-oxo-1,6-naphthyridine-3-carboxylate are heated at reflux in a mixture of 14.6 ml of acetic acid, 14.6 ml of water and 1.5 ml of concentrated sulphuric acid for two hours. The cooled mixture is put into ice-water, and the product is isolated and washed with water.

Yield: 3.6 g (88% of theory)
Melting point: 204°–206° C.

EXAMPLE G

9-Chloro-3-methyl-6-oxo-3,6-dihydro-2H-1-oxa-3a,8-diazaphenalene-5-carboxylic acid

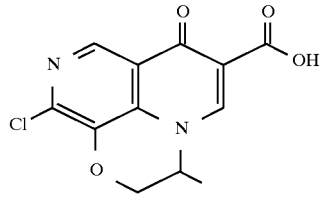

a. Ethyl 2-(4,5,-trichloronicotinoyl)-3-(1-hydroxy-2-propyl)amino-acrylate 5.0 g (0.014 mol) of ethyl 2-(4,5,6-trichloronicotinoyl)-3-ethoxyacrylate are placed at 0° C. in 21 ml of ethanol, and 1.16 g (0.0154 mol) of 2-aminopropanol are added dropwise. The mixture is stirred at room temperature for two hours, 45 ml of water are added, it is extracted with dichloromethane, and the extract is dried over sodium sulphate and concentrated on a rotary evaporator.

Yield: 5.3 g of crude product b. Ethyl 7,8-dichloro-1-(1-hydroxy-2-propyl)-1,4-dihydro-4-oxo-1,6-naphthyridine-3-carboxylate 5.2 g (0.014 mol) of ethyl 2-(4,5,6-trichloronicotinoyl)-3-(1-hydroxy-2-propyl)amino-acrylate are stirred with 2.3 g (0.0167 mol) of potassium carbonate in 28 ml of DMF at room temperature overnight. Ice-water is added to the mixture and the product is isolated. The mother liquor is extracted with chloroform and the organic phase is concentrated on a rotary evaporator. The crude products are stirred up with acetonitrile.

Yield: 2.42 g (51% of theory)
Melting point: 189°–192° C.

c. Ethyl 9-chloro-3-methyl-6-oxo-3,6-dihydro-2H-1-oxa-3a,8-diazaphenalene-5-carboxylate 2.42 g (0.007 mol) of ethyl 7,8-dichloro-1-(1-hydroxy-2-propyl)-1,4-dihydro-4-oxo-1,6-naphthyridine-3-carboxylate are heated with 1.15 g (0.0083 mol) of potassium carbonate in 14 ml of dimethylformamide at 80° C. for one hour. After addition of ice-water the precipitated product is isolated. The crude product is purified by column chromatography (eluent: dichloromethane/methanol 98:2).

Yield: 1.0 g (46% of theory)
Melting point: 185°–186° C.

d. 9-Chloro-3-methyl-6-oxo-3,6-dihydro-2H-1-oxa-3a,8-diazaphenalene-5-carboxylic acid 0.95 g (3.1 mmol) of ethyl 9-chloro-3-methyl-6-oxo-3,6-dihydro-2H-1-oxa-3a,8-diazaphenalene-5-carboxylate are heated at reflux in a mixture of 4 ml of acetic acid, 4 ml of water and 0.4 ml of concentrated sulphuric acid for four hours. The cooled mixture is put into ice-water, the product is isolated and washed with water.

Yield: 0.65 g (94% of theory)
Melting point: 218°–220° C. (with decomposition)

EXAMPLE H

7-Chloro-8-fluoro-1-(2,4-difluorophenyl)-1,4-dihydro-4-oxo-1,6-naphthyridine-3-carboxylic acid

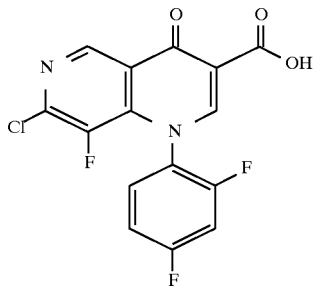

a. Ethyl 2-(4,6-dichloro-5-fluoronicotinoyl)-3-(2,4-difluorophenyl)amino-acrylate 6.72 g (0.02 mol) of ethyl 2-(4,6-dichloro-5-fluoronicotinoyl)-3-ethoxyacrylate are placed at 0° C. in 30 ml of ethanol, and a solution of 2.58 g (0.02 mol) of 2,4-difluoroaniline in 10 ml of ethanol is added dropwise. The mixture is stirred at room temperature for thirty minutes and cooled to 0° C. and the product which precipitates is isolated The crude product is washed with ethanol.

Yield: 4.5 g (55% of theory)
Melting point: 125° C.

b. Ethyl 7-chloro-8-fluoro-1-(2,4-difluorophenyl)-1,4-dihydro-4-oxo-1,6-naphthyridine-3-carboxylate 4.26 g (10 mmol) of ethyl 2-(4,6-dichloro-5-fluoronicotinoyl)-3-(2,4-difluorophenyl)amino-acrylate are stirred with 1.65 g (12 mmol) of potassium carbonate in 28 ml of DMF at 100° C. for four hours. Ice-water is added to the mixture and the product is isolated.

Yield: 3.55 g (93% of theory)
Melting point: 186° C.

c. 7-Chloro-8-fluoro-1-(2,4-difluorophenyl)-1,4-dihydro-4-oxo-1,6-naphthyridine-3-carboxylic acid 2.9 g (7.6 mmol) of ethyl 7-chloro-8-fluoro-1-(2,4-difluorophenyl)-1,4-dihydro-4-oxo-1,6-naphthyridine-3-carboxylate are heated at reflux in a mixture of 10 ml of acetic acid, 10 ml of water and 1 ml of concentrated sulphuric acid for two hours. The cooled mixture is put into ice-water, and the product is isolated and washed with water.

Yield: 2.4 g (92% of theory)
Melting point: 172°–174° C. (with decomposition)

EXAMPLE I 6,7-Dichloro-1-cyclopropyl-1,4-dihydro-5-methyl-4-oxo-1,6-naphthyridine-3-carboxylic acid

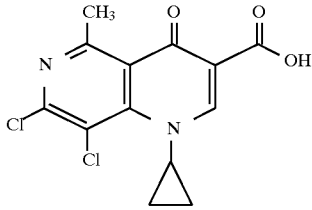

a. Ethyl 4,5,5-trichloro-3-hydroxy-2-(1-imino-ethyl)-penta-2,4-dienoate 383.6 g (1.98 mol) of trichloroacryloyl chloride are dissolved in 1068 ml of toluene, and 255.5 g (1.98 mol) of ethyl aminocrotonate in 156.7 g (1.98 mol) of pyridine are added dropwise at 10° C. After stirring at room temperature overnight, the mixture is washed 2× with 600 ml of water, and the organic phase is dried over sodium sulphate and concentrated under a high vacuum. The crude product is suspended in n-hexane and dried.

Yield: 406 g (70% of theory)
Melting point: 80° C.

b. Ethyl 5,6-dichloro-4-hydroxy-2-methyl-nicotinate 102.7 g (0.35 mol) of ethyl 4,5,5-trichloro-3-hydroxy-2-(1-imino-ethyl)penta-2,4-dienoate are heated at 180° C. in 1,2-dichlorobenzene for three hours. The volatile components are removed under a high vacuum up to 100° C. The residue is purified with dichloromethane on silica gel.

Yield: 71.8 g (65% of theory)

c. 5,6-Dichloro-4-hydroxy-2-methyl-nicotinic acid 36 g (0.14 mol) of ethyl 5,6-dichloro-4-hydroxy-2-methyl-nicotinate are boiled under reflux in 88 ml of ethanol and 175 ml of water with 24.2 g (0.43 mol) of potassium hydroxide for thirty minutes. The cooled mixture is brought to a pH of 1 with half-concentrated hydrochloric acid, while cooling with ice. The product which precipitates is isolated, washed with water and dried.

Yield: 31.5 g (98% of theory)
Melting point: 240° C.

d. 4,5,6-Trichloro-2-methyl-nicotinoyl chloride 30.4 g (0.14 mol) of 5,6-dichloro-4-hydroxy-2-methylnicotinic acid are heated slowly at reflux with 268 ml of phosphorus oxychloride and one drop of DMF. After two hours, the phosphorus oxychloride is distilled off in vacuo at about 100° C. The residue is put into ice-water and extracted with dichloromethane and the extract is dried over sodium sulphate and concentrated on a rotary evaporator.

The residue is heated at reflux in 165 ml of thionyl chloride for thirty minutes, the thionyl chloride is distilled off in vacuo, and the reside is distilled directly under a high vacuum.

Yield: 22.9 g (65% of theory)
Boiling point: 103° C. (0.6 mbar)

e. Ethyl 2-(4,5,6-trichloro-2-methylnicotinoyl)-acetate 31.55 g (0.18 mol) of potassium monoethyl malonate, 19.29 g (0.19 mol) of triethylamine and 21.56 g (0.23 mol) of magnesium chloride are placed in 272 ml of absolute acetonitrile and the mixture is stirred for two hours. Subsequently, 22.9 g (0.09 mol) of 4,5,6-trichloro-2-methyl-nicotinoyl chloride and 2.3 g (0.02 mol) of triethylamine are added dropwise at room temperature and the mixture is stirred overnight. The mixture is concentrated in vacuo and the residue is taken up in 135 ml of toluene and concentrated on a rotary evaporator.

The residue is again taken up in 135 ml of toluene, 130 ml of 13% strength hydrochloric acid are added dropwise with ice cooling. The mixture is stirred for 30 minutes and the phases are separated. The aqueous phase is extracted with toluene, and the combined organic phases are washed with water, dried over sodium sulphate and concentrated Yield: 29.2 g (100% of theory)

f. Ethyl 2-(4,5,6 -trichloro-2-methylnicotinoyl)-3-ethoxy-acrylate 29.2 g (0.09 mol) of ethyl 2-(4,5,6-trichloro-2-methyl-nicotinoyl-acetate are heated with 20.9 g (0.141 mol) of ethyl orthoformate and 23.9 g (0.23 mol) of acetic anhydride at 150°–160° C. for two hours. All volatile components are removed, initially in vacuo and then under a high vacuum up to 80° C.

Yield: 27 g (78% of theory)

g. Ethyl 2-(4,5,6-trichloro-2-methyl-nicotinoyl)-3-cyclopropylamino-acrylate 27 g (0.07 mol) of ethyl 2-(4,5,6-trichloro-2-methyl-nicotinoyl)-3-ethoxyacrylate are placed at 0° C. in 93 ml of ethanol, and 4.3 g (0.07 mol) of cyclopropylamine in 34 ml of ethanol are added dropwise. The mixture is stirred at room temperature for thirty minutes and cooled to 0° C. and the product which precipitates is isolated and washed with cold ethanol.

Yield: 14.3 g (52% of theory)
Melting point: 95° C.

h. Ethyl 7,8-dichloro-1-cyclopropyl-1,4-dihydro-5-methyl-4-oxo-1,6-naphthyridine-3-carboxylate 4.8 g (0.01 mol) of ethyl 2-(4,5,6-trichloro-2-methyl-nicotinoyl)-3-cyclopropylamino-acrylate are heated with 2.2 g (0.016 mol) of potassium carbonate in 40 ml of DMF at 100° C. for four hours. Ice-water is added to the cooled mixture and the product is isolated, washed with ice-water and dried.

Yield: 3 g (70% of theory)
Melting point: 172° C.

i. 7,8-Dichloro-1-cyclopropyl-1,4-dihydro-1,5-methyl-4-oxo-1,6-naphthyridine-3-carboxylic acid 6.2 g (0.018 mol) of ethyl 7,8-dichloro-1-cyclopropyl-1,4-dihydro-5-methyl-4-oxo-1,6-naphthyridine-3-carboxylate are heated at reflux in a mixture of 62 ml of acetic acid, 43 ml of water and 7.4 ml of concentrated sulphuric acid for two hours. The cooled mixture is put into ice-water and the product is isolated and washed with water.

Yield: 4.3 g (76% of theory)
Melting point: 212° C.

EXAMPLE J 7,8-Dichloro-1-[(1R,2S)-2-fluorocyclopropyl]-1,4-dihydro-5-methyl-4-oxo-1,6-naphthyridine-3-carboxylic acid

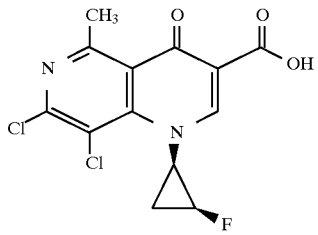

a. Ethyl 2-(4,5,6-trichloro-2-methyl-nicotinoyl)-3-[(1R,2S)-2-fluorocyclopropyl]-aminoacrylate 6.6 g (0.018 mol) of ethyl 2-(4,5,6-trichloro-2-methyl-nicotinoyl)-3-ethoxyacrylate and 2.0 g (0.018 mol) of (1R, 2S)-2-fluorocyclopropylamine hydrochloride are placed at 0° C. in a mixture of 27 ml of dichloromethane and 10.8 ml of water, and a solution of 1.5 g of sodium hydrogen carbonate in 18 ml of water is added dropwise. The mixture is stirred at room temperature for four hours, the phases are separated, and the organic phase is dried over sodium sulphate and concentrated on a rotary evaporator.

Yield: 7.0 g of crude product b. Ethyl 7,8-dichloro-1-[(1R,2S) -fluorocyclopropyl]-1,4-dihydro-5-methyl-4-oxo-1,6-naphthyridine-3-carboxylate 7.0 g (0.017 mol) of ethyl 2-(4,5,6-trichloro-2-methyl-nicotinoyl)-3-[(1R,2S)-2-fluorocyclopropyl]amino-acrylate are stirred with 2.8 g (0.020 mol) of potassium carbonate in 35 ml of DMF at room temperature overnight. Ice-water is added to the mixture and the product is isolated.

Yield: 5.1 g (81% of theory)

Melting point: 154°–155° C.

c. 7,8-Dichloro-1-[(1R,2S)-fluorocyclopropyl]-1,4-dihydro-5-methyl-4-oxo-1,6-naphthyridine-3-carboxylic acid 4.9 g (0.0136 mol) of ethyl 7,8-dichloro-1[(1R,2S)-2-fluorocyclopropyl]-1,4-dihydro-5-methyl-4-oxo-1,6-naphthyridine-3-carboxylate are heated at reflux in a mixture of 15.5 ml of acetic acid, 15.5 ml of water and 1.55 ml of concentrated sulphuric acid for two hours. The cooled mixture is put into ice-water, the product is isolated and washed with water, and the crude product is stirred with iso-propanol.

Yield: 2.6 g (57% of theory)

Melting point: 206°–207° C.

SYNTHESIS OF THE ACTIVE COMPOUNDS

EXAMPLE 1

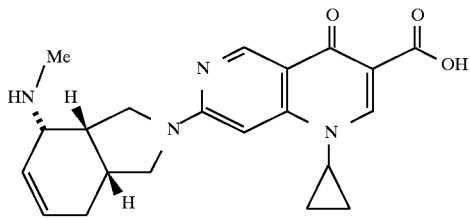

1-Cyclopropyl-1,4-dihydro-7-[(3aα,4β,7aα)-4-methylamino-1,3,3a,4,7,7a-hexahydroisoindol-2-yl]-4-oxo-1,6-naphthyridine-3-carboxylic acid 264.5 mg (1 mmol) of 7-chloro-1-cyclopropyl-1,4-dihydro-4-oxo-1,6-naphthyridine-3-carboxylic acid are heated at reflux with 334.5 mg (2.2 mmol) of (3aα,4β,7aα)-4-methylamino-1,3,3a,4,7,7aα-hexahydroisoindole in a mixture of 3 ml of dimethylformamide and 3 ml of acetonitrile for six hours. The precipitate is isolated and washed with acetonitrile.

Yield: 330 mg (86% of theory)

Melting point: 239°–240° C. (with decomposition)

EXAMPLE 2

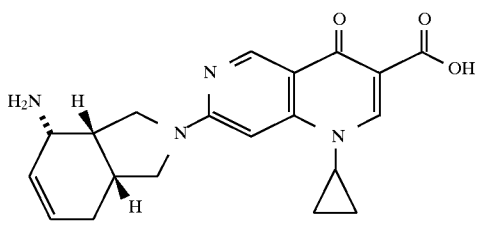

7-[3aα,4β,7aα)-4-Amino-1,3,3a,4,7,7a-hexahydroisoindol-2-yl]-1-cyclopropyl-1,4-dihydro-4-oxo-1,6-naphthyridine-3-carboxylic acid 264.5 mg (1 mmol) of 7-chloro-1-cyclopropyl-1,4-dihydro-4-oxo-1,6-naphthyridine-3-carboxylic acid are heated at reflux with 303 mg (2.2 mmol) of (3aα4β,7aα)-4-amino-1,3,3a,4,7,7a-hexahydroisoindole in a mixture of 3 ml of dimethylformamide and 3 ml of acetonitrile under nitrogen for eight hours. The precipitate is isolated and washed with acetonitrile.

Yield: 340 mg (92% of theory)

Melting point: 204°–206° C. (with decomposition)

EXAMPLE 3

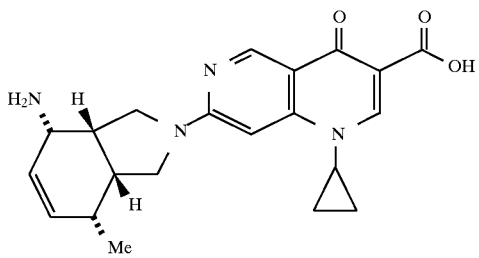

7-[(3aα,4β,7aα)-4-Amino-7-methyl-1,3,3a,4,7,7a-hexahydroisoindol-2-yl]-1-cyclopropyl-1,4-dihydro-4-oxo-1,6-naphthyridine-3-carboxylic acid 264.5 mg (1 mmol) of 7-chloro-1-cyclopropyl-1,4-dihydro-4-oxo-1,6-naphthyridine-3-carboxylic acid are heated at reflux with 330 mg (2.2 mmol) of (3aα,4β, 7aα)-4-amino-7-methyl-1,3,3a,4,7,7a-hexahydroisoindole in a mixture of 3 ml of dimethylformamide and 3 ml of acetonitrile under nitrogen for eight hours. The precipitate is isolated and washed with acetonitrile.

Yield: 296 mg (77% of theory)

Melting point: 204°–206° C. (with decomposition)

EXAMPLE 4

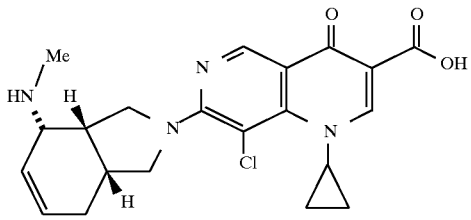

8-Chloro-1-cyclopropyl-1,4-dihydro-7-[(3aα,4β, 7aα)-4-methylamino-1,3,3a,4,7,7a-hexahydroisoindol-2-yl]-4-oxo-1,6-naphthyridine-3-carboxylic acid 299 mg (1 mmol) of 7,8-dichloro-1-cyclopropyl-1,4-dihydro-4-oxo-1,6-naphthyridine-3-carboxylic acid are heated at reflux with 334.5 mg (2.2 mmol) of (3aα,4β,7aα)-4-methylamino-1,3,3a,4,7,7a-hexahydroisoindole in a mixture of 3 ml of dimethylformamide and 3 ml of acetonitrile under nitrogen for four hours. The precipitate is isolated and washed with acetonitrile.

Yield: 380 mg (91% of theory)

Melting point: 210°–212° C. (with decomposition)

EXAMPLE 5

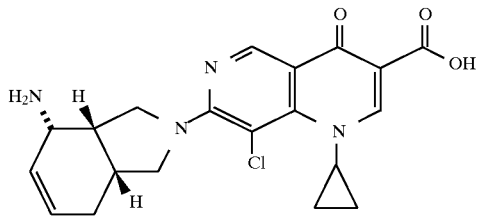

7-[(3aα,4β,7aα)-4-Amino-1,3,3a,4,7,7a-hexahydroisoindol-2-yl]-8-chloro-1-cyclopropyl-1,4-dihydro-4-oxo-1,6-naphthyridine-3-carboxylic acid 1.05 g (3.5 mmol) of 7,8-dichloro-1-cyclopropyl-1,4-dihydro-4-oxo-1,6-naphthyridine-3-carboxylic acid are heated at reflex with 1063 g (7.7 mmol) of (3aα,4β,7aα)-4-amino-1,3,3a,4,7,7a-hexahydroisoindole in a mixture of 11 ml of dimethylformamide and 11 ml of acetonitrile under nitrogen for eight hours. The precipitate is isolated and stirred up with water.

Yield: 1.35 g (96% of theory)

Melting point: 193°–195° C. (with decomposition)

EXAMPLE 6

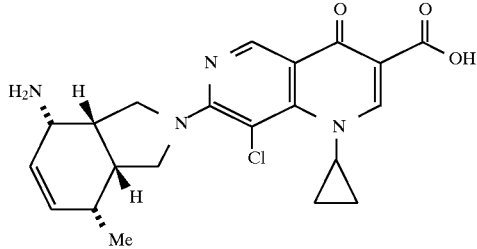

7-[(3aα,4β,7β7aα)-4-Amino-7-methyl-1,3,3a,4,7,7a-hexahydroisoindol-2-yl]-8-chloro-1-cyclopropyl-1,4-dihydro-4-oxo-1,6-naphthyridine-3-carboxylic acid 1.05 g (3.5 mmol) of 7,8-dichloro-1-cyclopropyl-1,4-dihydro-4-oxo-1,6-naphthyridine-3-carboxylic acid are heated at reflux with 1.17 g (7.7 mmol) of (3aα, 4β,7β,7aα)-4-amino-7-methyl-1,3,3a,4,7,7a-hexahydroisoindole in a mixture of 11 ml of dimethylformamide and 11 ml of acetonitrile under nitrogen for six hours. The precipitate is isolated and stirred up with water.

Yield: 1.2 g (82% of theory)

Melting point: 210°–212° C. (with decomposition)

EXAMPLE 7

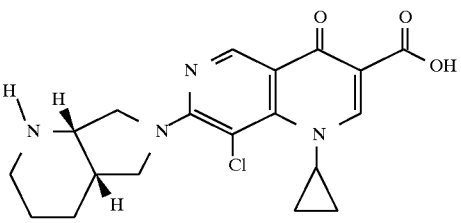

8Chloro-1-cyclopropyl-1,4-dihydro-7-[(1S,6S)-2,8-diazabicyclo[4.3.0]nonan-8-yl]-4-oxo-1,6-naphthyridine-3-carboxylic acid 200 mg (0.67 mmol) of 7,8-dichloro-1-cyclopropyl-1,4-dihydro-4-oxo-1,6-naphthyridine-3-carboxylic acid are stirred with 190 mg (1.5 mmol) of (1S,6S)-2,8-diazabicyclo[4.3.0]nonane in a mixture of 1.7 ml of dimethylformamide and 1.7 ml of acetonitrile under argon overnight. The precipitate is isolated and washed with acetonitrile. The crude product is purified on silica gel (eluent: dichloromethane/methanol/aqueous ammonia solution 75:20:25).

Yield: 56 mg (21% of theory)

EXAMPLE 8

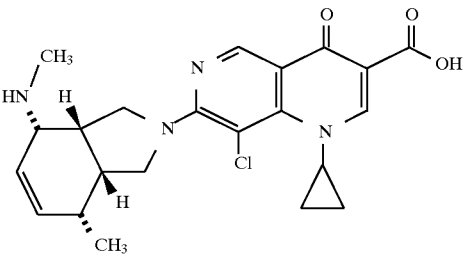

8-Chloro-1-cyclopropyl-1,4-dihydro-7-[(3aα,4β,7β,7aα)-7-methyl-4-methylamino- 1,3,3a,4,7,7a-hexahydroisoindol-2-yl]-4-oxo-1,6-naphthyridine-3-carboxy acid 299 mg (1 mmol) of 7,8-dichloro-1-cyclopropyl-1,4-dihydro-4-oxo-1,6-naphthyridine-3-carboxylic acid are heated at reflux with 360 mg (2.2 mmol) of (3aα,4β,7β,7aα)-7-methyl-4-methylamino-1,3,3a,4,7,7a-hexahydroisoindole in a mixture of 3 ml of dimethylformamide and 3 ml of acetonitrile under nitrogen for nine hours. The precipitate is isolated and washed with acetonitrile. The crude product is stirred up thoroughly with water.

Yield: 330 mg (76% of theory)

Melting point: 196°–198° C. (with decomposition)

EXAMPLE 9

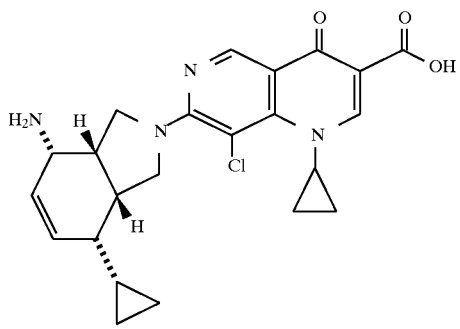

7-[(3aα,4β,7β,7aα)-4-amino-7-cyclopropyl-1,3,3a,4,
7,7a-hexahydroisoindol-2-yl]-8-chloro-1-
cyclopropyl-1,4-dihydro-4-oxo-1,6-naphthyridine-3-
carboxylic acid 200 mg (0.67 mmol) of 7,8-dichloro-1-cyclopropyl-1,4-dihydro-4-oxo-1,6-naphthyridine-3-carboxylic acid are heated at reflux with 260 mg (1.5 mol) of (3aα,4β,7β,7aα)-4-amino-7-cyclopropyl-1,3,3a,4,7,7a-hexahydroisoindole in a mixture of 1.7 ml of dimethylformamide and 1.7 ml of acetonitrile under argon for nine hours. The precipitate is isolated, washed with acetonitrile and stirred up with water.

Yield: 125 mg (43% of theory)

Melting point: 229°–230° C. (with decomposition)

EXAMPLE 10

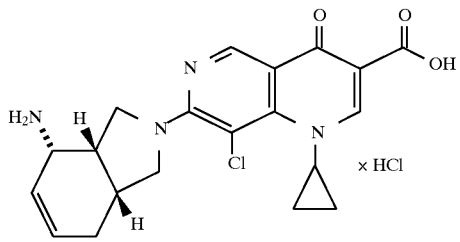

7-[(3aα,4β,7aα)-4-Amino-1,3,3a,4,7,7a-
hexahydroisoindol-2-yl]-8-chloro-1-cyclopropyl-1,4-
dihydro-4-oxo-1,6-naphthyridine-3-carboxylic acid
hydrochloride 6.1 g (0.015 mol) of 7-[(3aα,4β,7aα)-4-amino-1,3,3a,4,7,7a-hexahydroisoindol-2-yl]-8-chloro-1-cyclopropyl-1,4-dihydro-4-oxo-1,6-naphthyridine-3carboxylic acid are heated in 180 ml of half-concentrated hydrochloric acid until dissolution is complete. The excess hydrochloric acid is removed in vacuo and the residue is stirred up with acetonitrile.

Yield: 6.3 g (96% of theory)

Melting point: 238°–240° C. (with decomposition)

EXAMPLE 11

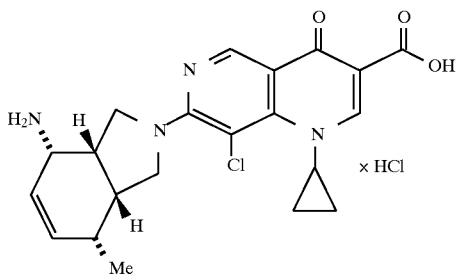

7-[(3aα,4β,7β,7aα)-4-Amino-7-methyl-1,3,3a,4,7,
7a-hexahydroisoindol-2-yl]-8-chloro-1-cyclopropyl-
1,4-dihydro-4-oxo-1,6-naphthyridine-3-carboxylic
acid hydrochloride Similarly to Example 10, the title compound is obtained when 7-[(3aα,4β,7β,7aα)-4-amino-7-methyl-1,3,3a,4,7,7a-hexahydroisoindol-2-yl]-8-chloro-1-cyclopropyl-1,4-dihydro-4-oxo-1,6-naphthyridine-3-carboxylic acid is reacted.

Melting point: 190°–192° C. (with decomposition)

EXAMPLE 12

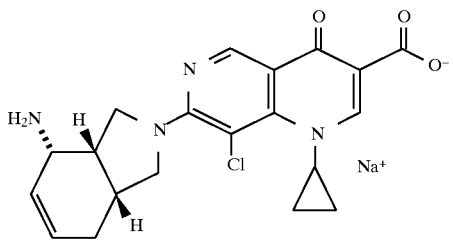

Sodium [7-[(3aα,4β,7aα)-4-amino-1,3,3a,4,7,7a-
hexahydroisoindol-2-yl]-8-chloro-1-cyclopropyl-1,4-
dihydro-4-oxo-1,6-naphthyridine-3-carboxylate]

240 mg (0.6 mmol) of 7-[(3aα,4β,7aα)-4-amino-1,3,3a,4,7,7a-hexahydroisoindol-2-yl)-8-chloro-1-cyclopropyl-1,4-dihydro-4-oxo-1,6-naphthyridine-3-carboxylic acid are heated in 30 ml of water and 0.6 ml (0.6 mmol) of 1N sodium hydroxide solution until dissolution is complete. The excess water is removed in vacuo and the residue is stirred up with ethanol.

Yield: 210 mg (84% of theory)

Melting point: >300° C.

EXAMPLE 13

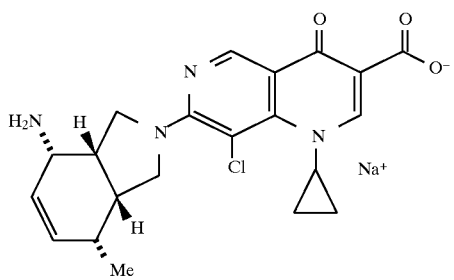

Sodium [7-[(3aα,4β,7β,7aα)-4-amino-7-methyl-1,3,3a,4,7,7a-hexahydro-isoindol-2yl]-8-chloro-1-cyclopropyl-1,4-dihydro-4-oxo-1,6-naphthyridine-3-carboxylate]

Similarly to Example 12, the title compound is obtained when 7-[(3aα,4β,7β,7aα)-4-amino-7-methyl-1,3,3a,4,7,7a-hexahydroisoindol-2-yl)-8-chloro-1-cyclopropyl-1,4-dihydro-4-oxo-1,6-naphthyridine-3-carboxylic acid is reacted.

Melting point: 230°–232° C. (with decomposition)

EXAMPLE 14

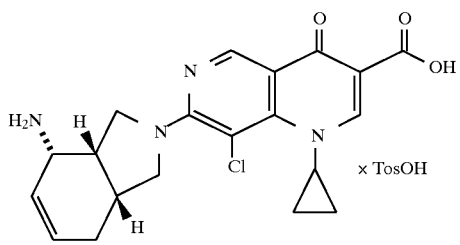

7-[(3aα,4β,7aα)-4-amino-1,3,3a,4,7,7a-hexahydroisoindol-2-yl]-8-chloro-1cyclopropyl-1,4-dihydro-4-oxo-1,6-naphthyridine-3-carboxylic acid tosylate 240 mg (0.6 mmol) of 7-[(3aα,4β,7aα)-4-amino-3,3a,4,7,7a-hexahydroisoindol-2-8-chloro-1-cyclopropyl-1,4-dihydro-4-oxo-1,6-naphthyridine-3-carboxylic acid are heated with 114 mg (0.6 mmol) of p-toluenesulphonic acid in 30 ml of water until dissolution is complete. The water is removed in vacuo and the product is dried.

Yield: 240 mg (70% of theory)

Melting point: 296°–298° C. (with decomposition)

EXAMPLE 15

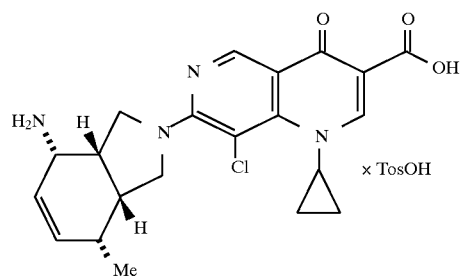

7-[(3aα,4β,7β,7aα)-4-amino-7-methyl-1,3,3a,4,7,7a-hexahydroisoindol-2-yl]-8-chloro-1-cyclopropyl-1,4-dihydro-4-oxo-1,6-naphthyridine-3-carboxylic acid tosylate Similarly to Example 14, the title compound is obtained when 7-[(3aα,4β,7β,7aα)-4-amino-7-methyl-1,3,3a,4,7,7a-hexahydroisoindol-2-yl)-8-chloro-1-cyclopropyl-1,4-dihydro-4-oxo-1,6-naphthyridine-3-carboxylic acid is reacted.

Melting point: 288°–290° C. (with decomposition)

EXAMPLE 16

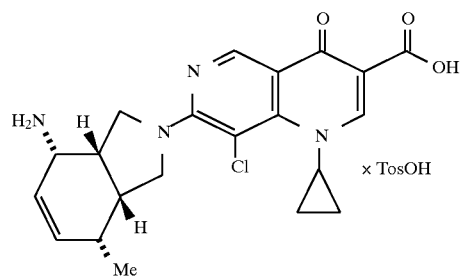

7-[(3aα,4β,7aα)-4-amino-1,3,3a,4,7,7a-hexahydroisoindol-2-yl]-8-chloro-1-cyclopropyl-1,4-dihydro-4-oxo-1,6-naphthyridine-3-carboxylic acid hydrobromide 240 mg (0.6 mmol) of 7-[(3aα,4β,7aα)-4-amino-1,3,3a,4,7,7a-hexahydro-isoindol-2-yl)-8-chloro-1-cyclopropyl-1,4-dihydro-4-oxo-1,6-naphthyridine-3-carboxylic acid are heated with 100 mg (0.6 mmol) of 48% strength hydrobromic acid in 30 ml of water until dissolution is complete. The water is removed in vacuo and the product is stirred up with ethanol.

Yield: 270 mg (70% of theory)

Melting point: 236°–238° C. (with decomposition)

EXAMPLE 17

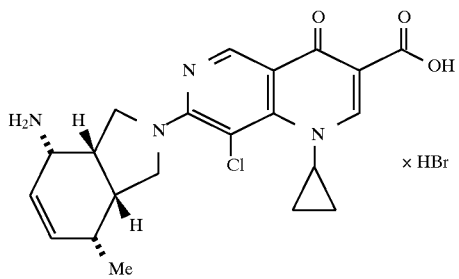

7-[(3aα,4β,7β,7aα)-4-amino-7-methyl-1,3,3a,4,7,7a-hexahydroisoindol-2-yl]-8-chloro-1-cyclopropyl-1,4-dihydro-4-oxo-1,6-naphthyridine-3-carboxylic acid hydrobromide Similarly to Example 16, the title compound is obtained when 7-[(3aα,4β,7β,7aα)-4-amino-7-methyl-1,3,3a,4,7,7a-hexahydroisoindol-2-yl)-8-chloro-1-cyclopropyl-1,4-dihydro-4-oxo-1,6-naphthyridine-3-carboxylic acid is reacted.

Melting point: 228°–230° C. (with decomposition)

EXAMPLE 18

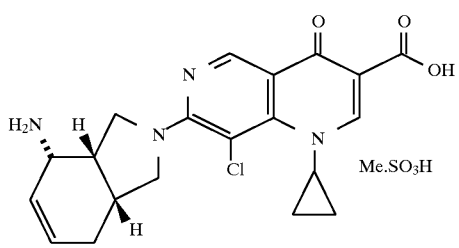

7-[(3aα,4β,7aα)-4-amino-1,3,3a,4,7,7a-hexahydroisoindol-2-yl]-8-chloro-1-cyclopropyl-1,4-dihydro-4-oxo-1,6-naphthyridine-3-carboxylic acid mesylate 240 mg (0.6 mmol) of 7-[(3aα,4β,7aα)-4-amino-1,3,3a, 4,7,7a-hexahydro-isoindol-2-yl)-8-chloro-1-cyclopropyl-1, 4-dihydro-4-oxo-1,6-naphthyridine-3-carboxylic acid are boiled under reflux with 57.6 mg (0.6 mmol) of methanesulphonic acid in 5 ml of methanol for five minutes. Stirring is continued overnight, the methanol is removed in vacuo and the product is stirred up with ethanol.

Yield: 270 mg (90% of theory)

Melting point: 220°–222° C. (with decomposition)

EXAMPLE 19

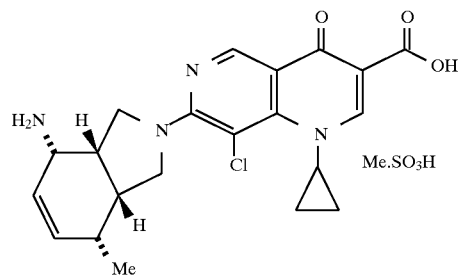

7-[(3aα,4β,7β,7aα)-4-amino-1,3,3a,4,7,7a-hexahydroisoindol-2-yl]-8-chloro-1-cyclopropyl-1,4-dihydro-4-oxo-1,6-naphthyridine-3-carbolic acid mesylate Similarly to Example 18, the title compound is obtained when 7-[(3aα,4β,7β,7aα)-4-amino-7-methyl-1,3,3a,4,7,7a-hexahydroisoindol-2-yl)-8-chloro-1-cyclopropyl-1,4-dihydro-4-oxo-1,6-naphthyridine-3-carboxylic acid is reacted.

Melting point: 218°–220° C. (with decomposition)

EXAMPLE 20

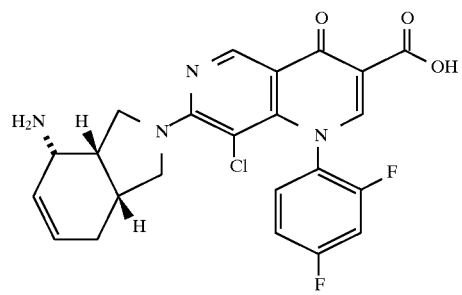

7-[(3aα,4β,7aα)-4-amino-1,3,3a,4,7,7a-hexahydroisoindol-2-yl]-8-chloro-1-(2,4-difluorophenyl)-1,4-4-oxo-1,6-naphthyridine-3-carboxylic acid 372 mg (1 mmol) of 7,8-dichloro-1-(2,4-difluorophenyl)-1,4-dihydro-4-oxo-1,6-naphthyridine-3-carboxylic acid are stirred with 300 mg (2.2 mmol) of (3aα,4β,7aα)-4-amino-1,3,3a,4,7,7a-hexahydroisoindole in a mixture of 3 ml of dimethylformamide and 3 ml of acetonitrile under nitrogen at room temperature overnight. The precipitate is isolated and stirred with acetonitrile.

Yield: 400 mg (85% of theory)

Melting point: 262°–263° C. (with decomposition)

EXAMPLE 21

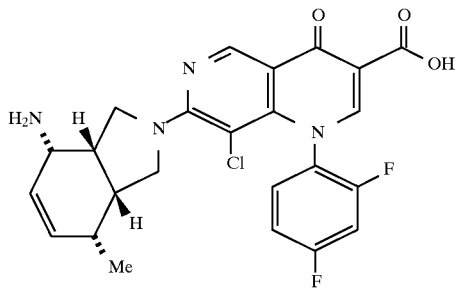

7-[(3aα,4β,7β,7aα)-4-amino-7-methyl-1,3,3a,4,7,7a-hexahydroisoindol-2-yl]-8-chloro-1-(2,4-difluorophenyl)-1,4-dihydro-4-oxo-1,6-naphthyridine-3-carboxylic acid 372 mg (1 mmol) of 7,8-dichloro-1-(2,4-difluorophenyl)-1,4-dihydro-4-oxo-1,6-naphthyridine-3-carboxylic acid are stirred with 330 mg (2.2 mmol) of (3aα,4β,7β,7aα)-4-amino-7-methyl-1,3,3a,4,7,7a-hexahydroisoindole in a mixture of 3 ml of dimethylformamide and 3 ml of acetonitrile under nitrogen at 60° C. for four hours. Water is added to the mixture, and the precipitate is isolated and stirred up with acetonitrile.

Yield: 400 mg (86% of theory)

Melting point: 258°–260° C. (with decomposition)

EXAMPLE 22

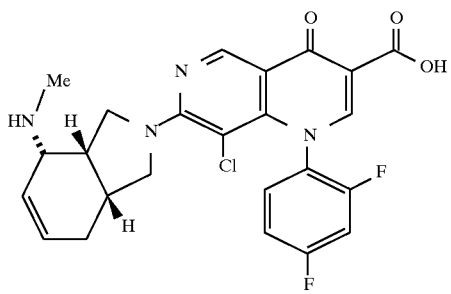

8-Chloro-1-(2,4-difluorophenyl)-1,4-dihydro-7-[(3aα,4β,7aα)-4-methylamino-1,3,3a,4,7,7a-hexahydroisoindol-2-yl]-4-oxo-1,6-naphthyridine-3-carboxylic acid 372 mg (1 mmol) of 7,8-dichloro-1-(2,4-difluorophenyl)-1,4-dihydro-4-oxo-1,6-naphthyridine-3-carboxylic acid are stirred with 330 mg (2.2 mmol) of (3aα,4β,7aα)-4-methylamino-1,3,3a,4,7,7a-hexahydroisoindole in a mixture of 3 ml of dimethylformamide and 3 ml of acetonitrile under nitrogen at 60° C. for four hours. The precipitate is isolated and washed with acetonitrile.

Yield: 420 mg (86% of theory)

Melting point: 254°–256° C. (with decomposition)

EXAMPLE 23

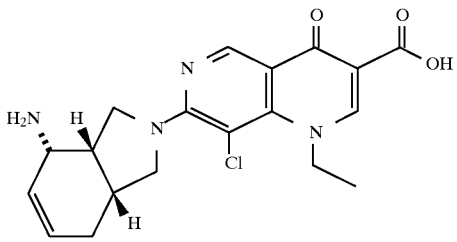

7-[(3aα,4β,7aα)-4-Amino-1,3,3a,4,7,7a-hexahydroisoindol-2-yl]-8-chloro-1-ethyl-1,4-dihydro-4-oxo-1,6-naphthyridine-3-carboxylic acid 287 mg (1 mmol) of 7,8-dichloro-1-ethyl-1,4-dihydro-4-oxo-1,6-naphthyridine-3-carboxylic acid are stirred with 300 mg (2.2 mmol) of (3aα,4β,7aα)-4-amino-1,3,3a,4,7,7a-hexahydroisoindole in a mixture of 3 ml of dimethylformamide and 3 ml of acetonitrile under nitrogen at 60° C. for six hours. Ice-water is added to the mixture, and the precipitate is isolated and stirred with acetonitrile.

Yield: 340 mg (87% of theory)

Melting point: 244°–245° C. (with decomposition)

EXAMPLE 24

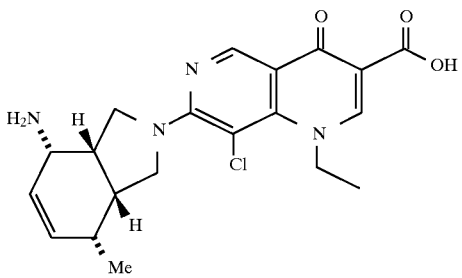

7-[(3aα,4β,7β,7aα)-4-amino-7-methyl-1,3,3a,4,7,7a-hexahydroisoindol-2-yl]-8-chloro-1-ethyl-1,4-dihydro-4-oxo-1,6-naphthyridine-3-carboxylic acid 287 mg (1 mmol) of 7,8-dichloro-1-ethyl-1,4-dihydro-4-oxo-1,6-naphthyridine-3-carboxylic acid are stirred with 330 mg (2.2 mmol) of (3aα,4β,7β,7aα)-4-amino-7-methyl-1,3,3a,4,7,7a-hexahydroisoindole in a mixture of 3 ml of dimethylformamide and 3 ml of acetonitrile under nitrogen at 60° C. for six hours. Ice-water is added to the mixture, and the precipitate is isolated and stirred up with acetonitrile.

Yield: 360 mg (89% of theory)

Melting point: 231°–233° C. (with decomposition)

EXAMPLE 25

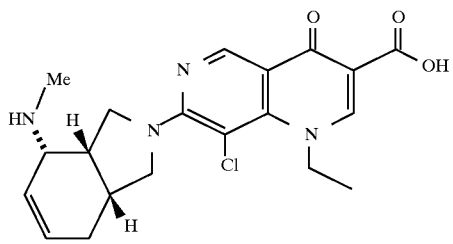

8-Chloro-1-ethyl-1,4-dihydro-7-[(3aα,4β,7aα)-4-methylamino-1,3,3a,4,7,7a-hexahydroisoindol-2-yl]-4-oxo-1,6-naphthyridine-3-carboxylic acid 287 mg (1 mmol) of 7,8-dichloro-1-ethyl-1,4-dihydro-4-oxo-1,6-naphthyridine-3-carboxylic acid are stirred with 330 mg (2.2 mmol) of (3aα,4β,7aα)-4-methylamino-1,3,3a,4,7,7a-hexahydroisoindole in a mixture of 3 ml of dimethylformamide and 3 ml of acetonitrile under nitrogen at 60° C. for two hours. The precipitate is isolated and washed with acetonitrile.

Yield: 380 mg (94% of theory)

Melting point: >300° C. (with decomposition)

EXAMPLE 26

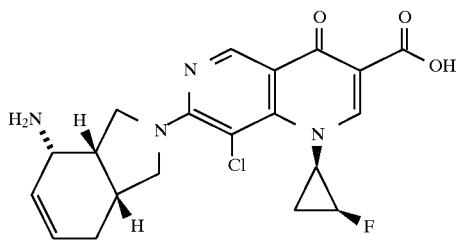

7-[(3aα,4β,7aα)-4-Amino-1,3,3a,4,7,7a-hexahydroisoindol-2-yl]-8-chloro-1-(cis-2-fluorocyclopropyl)-1,4-dihydro-4-oxo-1,6-naphthyridine-3-carboxylic acid 317 mg (1 mmol) of 7,8-dichloro-1-(cis-2-fluorocyclopropyl)-1,4-dihydro-4-oxo-1,6-naphthyridine-3-carboxylic acid are stirred with 300 mg (2.2 mmol) of (3aα,4β,7aα)-4-amino-1,3,3a,4,7,7a-hexahydroisoindole in a mixture of 3 ml of dimethylformamide and 3 ml of acetonitrile under nitrogen at 60° C. for two hours. Ice-water is added to the mixture, the pH is adjusted to 7 with dilute hydrochloric acid, and the precipitate is isolated and stirred up with acetonitrile.

Yield: 310 mg (74% of theory)

Melting point: 229°–230° C. (with decomposition)

EXAMPLE 27

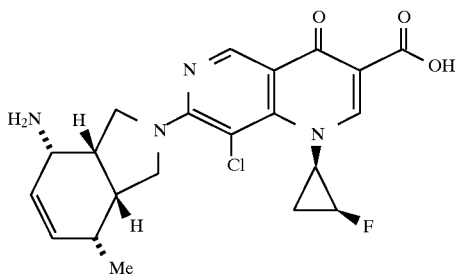

7-(3aα,4β,7β,7aα)-4-Amino-7-methyl-1,3,3a,4,7,7a-hexahydroisoindol-2-yl]-8-chloro-1-(cis-2-fluorocyclopropyl)-1,4-dihydro-4-oxo-1,6-naphthyridine-3-carboxylic acid 317 mg (1 mmol) of 7,8-dichloro 1-(cis-2-fluorocyclopropyl)-1,4-dihydro-4-oxo-1,6-naphthyridine-3-carboxylic acid are stirred with 330 mg (2.2 mmol) of (3aα,4β,7β,7aα)-4-amino-7-methyl-1,3,3a,4,7,7a-hexahydroisoindole in a mixture of 3 ml of dimethylformamide and 3 ml of acetonitrile under nitrogen at 60° C. for six hours. Ice-water is added to the mixture, and the precipitate is isolated and stirred up with acetonitrile.

Yield: 330 mg (76% of theory)

Melting point: 206°–208° C. (with decomposition)

EXAMPLE 28

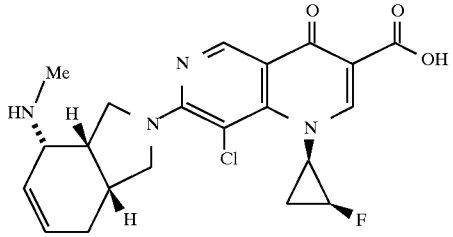

8-Chloro-1-(cis-2-fluorocyclopropyl)-1,4-dihydro-7-[(3aα,4β,7aα)-4-methylamino-1,3,3a,4,7,7a-hexahydroisoindol-2-yl]-4-oxo-1,6-naphthyridine-3-carboxylic acid 317 mg (1 mmol) of 7,8-dichloro-1-(cis-2-fluorocyclopropyl)-1,4-dihydro-4-oxo-1,6-naphthyridine-3-carboxylic acid are stirred with 330 mg (2.2 mmol) of (3aα,4β,7aα)-4-methylamino-1,3,3a,4,7,7a-hexahydroisoindole in a mixture of 3 ml of dimethylformamide and 3 ml of acetonitrile under nitrogen at 60° C. for two hours. The precipitate is isolated and washed with acetonitrile.

Yield: 370 mg (85% of theory)

Melting point: 199°–200° C. (with decomposition)

EXAMPLE 29

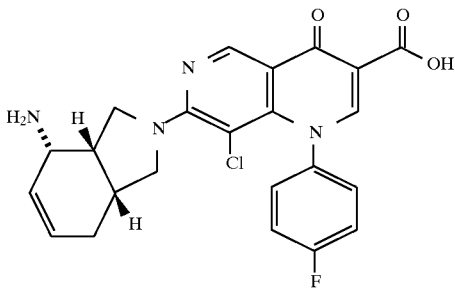

7-[(3aα,4β,7aα)-4-Amino-1,3,3a,4,7,7a-hexahydroisoindol-2-yl]-8-chloro-1-(4-fluorophenyl)-1,4-dihydro-4-oxo-1,6-naphthyridine-3-carboxylic acid 353 mg (1 mmol) of 7,8-dichloro-1-(4-fluorophenyl)-1,4-dihydro-4-oxo-1,6-naphthyridine-3-carboxylic acid are stirred with 300 mg (2.2 mmol) of (3aα,4β,7aα)-4-amino-1,3,3a,4,7,7a-hexahydroisoindole in a mixture of 3 ml of dimethylformamide and 3 ml of acetonitrile under nitrogen at 60° C. for ten hours. Ice-water is added to the mixture, and the precipitate is isolated and stirred up with acetonitrile.

Yield: 410 mg (90% of theory)

Melting point: 279°–280° C. (with decomposition)

EXAMPLE 30

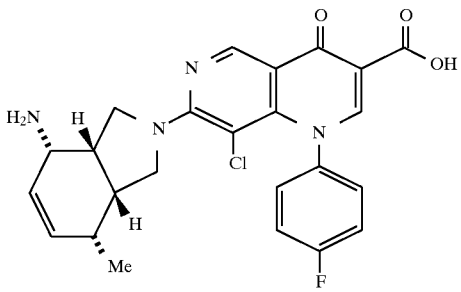

7-[(3aα,4β,7β,7aα)-4-Amino-7-methyl-1,3,3a,4,7,7a-hexahydroisoindol-2-yl]-8-chloro-1-(4-fluorophenyl)-1,4-dihydro-4-oxo-1,6-naphthyridine-3-carboxylic acid 353 mg (1 mmol) of 7,8-dichloro-1-(4-fluorophenyl)-1,4-dihydro-4-oxo-1,6-naphthyridine-3-carboxylic acid are stirred with 330 mg (2.2 mmol) of (3aα,4β,7β,7aα)-4-amino-7-methyl-1,3,3a,4,7,7a-hexahydroisoindole in a mixture of 3 ml of dimethylformamide and 3 ml of acetonitrile under nitrogen at 80° C. for 16 hours. Ice-water is added to the mixture, and the precipitate is isolated and stirred up with acetonitrile.

Yield: 400 mg (86% of theory)

Melting point: 251°–253° C. (with decomposition)

EXAMPLE 31

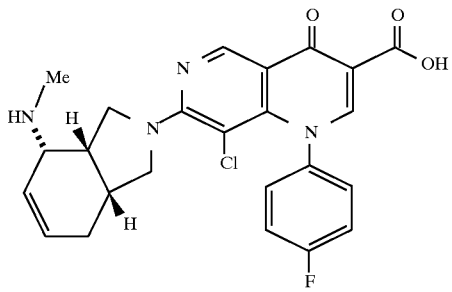

8-Chloro-1-(4-fluorophenyl)-1,4-dihydro-7-[(3aα,4β,7aα)-4-methylamino-1,3,3a,4,7,7a-hexahydroisoindol-2-yl]-4-oxo-1,6-naphthyridine-3-carboxylic acid 353 mg (1 mmol) of 7,8-dichloro-1-(4-fluorophenyl)-1,4-dihydro-4-oxo-1,6-naphthyridine-3-carboxylic acid are stirred with 330 mg (2.2 mmol) of (3aα,4β,7aα)-4-methylamino-1,3,3a,4,7,7a-hexahydroisoindole in a mixture of 3 ml of dimethylformamide and 3 ml of acetonitrile under nitrogen at 60° C. for ten hours. The precipitate is isolated and washed with acetonitrile.

Yield: 410 mg (88% of theory)

Melting point: 238°–240° C. (with decomposition)

EXAMPLE 32

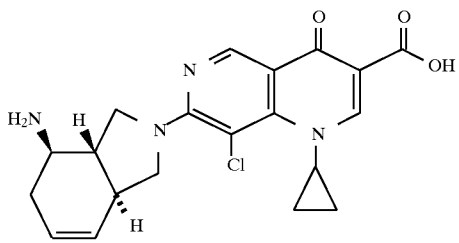

7-[(3aα,4β,7β)-4-Amino-1,3,3a,4,5,7a-hexahydroisoindol-2-yl]-8-chloro-1-cyclopropyl-1,4-dihydro-4-oxo-1,6-naphthyridine-3-carboxylic acid hydrochloride 1.05 g (3.5 mmol) of 7,8-dichloro-1-cyclopropyl-1,4-dihydro-4-oxo-1,6-naphthyridine-3-carboxylic acid are stirred with 1.62 g (7.7 mmol) of (3aα,4β,7aβ)-4-ethoxycarbonylamino-1,3,3a,4,5,7a-hexahydroisoindole in a mixture of 10.5 ml of dimethylformamide and 10.5 ml of acetonitrile under nitrogen at 80° C. for eight hours. After cooling, the precipitate is isolated and stirred up with acetonitrile.

The residue (1.2 g) is heated in 25 ml of 10% strength potassium hydroxide solution and 12.5 ml of ethylene glycol at 130° C. for six hours. 25 ml of methanol are added to the cooled mixture, and the pH is adjusted to 4–5 with dilute hydrochloric acid. The solid which precipitates is isolated and taken up again in a mixture of 17.5 ml of methanol and 17.5 ml of water. The pH is adjusted to 2–3 with concentrated hydrochloric acid, and the solid is isolated and stirred up with acetonitrile.

Yield: 600 mg (42% of theory)

Melting point: 259°–260° C. (with decomposition)

EXAMPLE 33

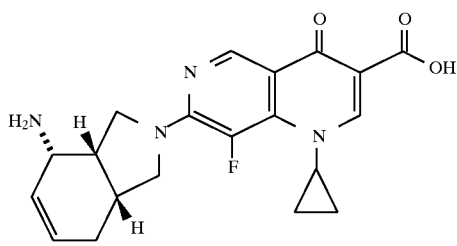

7-[(3aα,4β,7aα)-4-Amino-1,3,3a,4,7,7a-hexahydroisoindol-2-yl]-1-cyclopropyl-8-fluoro-1,4-dihydro-4-oxo-1,6-naphthyridine-3-carboxylic acid 282 mg (1 mmol) of 7-chloro-1-cyclopropyl-8-fluoro-1,4-dihydro-4-oxo-1,6-naphthyridine-3-carboxylic acid are stirred with 303 mg (2.2 mmol) of (3aα,4β,7aα)-4-amino-1,3,3a,4,7,7a-hexahydroisoindole in a mixture of 3 ml of dimethylformamide and 3 ml of acetonitrile under nitrogen at 80° C. for six hours. After the mixture has cooled, ice-water is added and the precipitate is isolated and stirred up with acetonitrile.

Yield: 340 mg (88% of theory)

Melting point: 259°–260° C. (with decomposition)

EXAMPLE 34

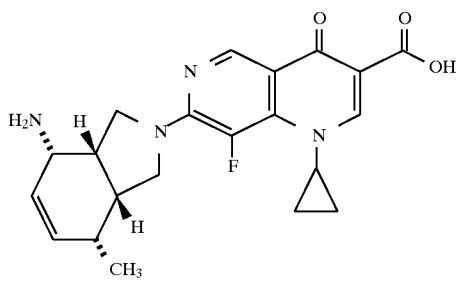

7-[(3aα,4β,7β,7aα)-4-Amino-7-methyl-1,3,3a,4,7,7a-hexahydroisoindol-2-yl]-1-cyclopropyl-8-fluoro-1,4-dihydro-4-oxo-1,6-naphthyridine-3carboxylic acid 282 mg (1 mmol) of 7-chloro-1-cyclopropyl-8-fluoro-1,4-dihydro-4-oxo-1,6-naphthyridine-3-carboxylic acid are stirred with 330 mg (2.2 mmol) of (3aα,4β,7β,7aα)-4-amino-7-methyl-1,3,3a,4,7,7a-hexahydroisoindole in a mixture of 3 ml of dimethylformamide and 3 ml of acetonitrile under nitrogen at 80° C. for six hours. After the mixture has cooled, ice-water is added and the precipitate is isolated and stirred up with acetonitrile.

Yield: 310 mg (77% of theory)

Melting point: 230°–232° C. (with decomposition)

EXAMPLE 35

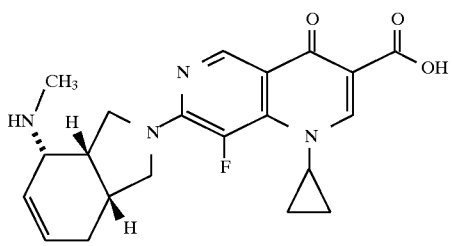

1-Cyclopropyl-8-fluoro-1,4-dihydro-7-[(3aα,4β,7aα)-4-methylamino-1,3,3a,4,7,7a-hexahydroisoindol-2-yl]-4-oxo-1,6-naphthyridine-3-carboxylic acid 282 mg (1 mmol) of 7-chloro-1-cyclopropyl-8-fluoro-1,4-dihydro-4-oxo-1,6-naphthyridine-3-carboxylic acid are stirred with 330 mg (2.2 mmol) of (3aα,4β,7aα)-4-methylamino-1,3,3a,4,7,7a-hexahydroisoindole in a mixture of 3 ml of dimethylformamide and 3 ml of acetonitrile under nitrogen at 80° C. for two hours. After the mixture has cooled, ice-water is added and the precipitate is isolated and stirred up with acetonitrile.

Yield: 290 mg (72% of theory)

Melting point: 231°–233° C. (with decomposition)

EXAMPLE 36

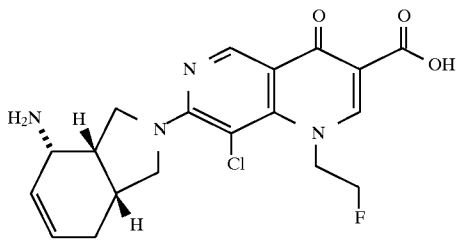

7-[(3aα,4β,7aα)-4-Amino-1,3,3a,4,7,7a-hexahydroisoindol-2-yl]-8-chloro-1-(2-fluoroethyl)-1,4-oxo-1,6-naphthyridine-3-carboxylic acid 305 mg (1 mmol) of 7,8-dichloro-1-(2-fluoroethyl)-1,4-dihydro-4-oxo-1,6-naphthyridine-3-carboxylic acid are stirred with 303 mg (2.2 mmol) of (3aα,4β,7aα)-4-amino-1,3,3a,4,7,7a-hexahydroisoindole in a mixture of 3 ml of dimethylformamide and 3 ml of acetonitrile under nitrogen at 80° C. for four hours. After the mixture has cooled, ice-water is added and the precipitate is isolated and stirred up with acetonitrile.

Yield: 340 mg (83% of theory)

Melting point: 241°–242° C. (with decomposition)

EXAMPLE 37

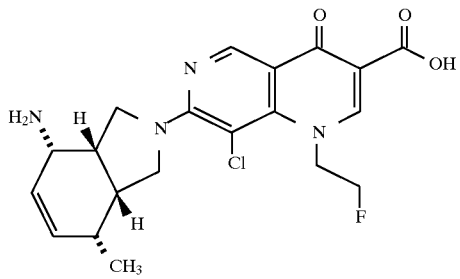

7-[(3aα,4β,7β,7aα)-4-Amino-7-methyl-1,3,3a,4,7,
7a-hexahydroisoindol-2-yl]-8-chloro-1-(2-
fluoroethyl)-1,4-dihydro-4-oxo-1,6-naphthyridine-3-
carboxylic acid 305 mg (1 mmol) of 7,8-dichloro-1-(2-fluoroethyl)-1,4-dihydro-4-oxo-1,6-naphthyridine-3-carboxylic acid are stirred with 330 mg (2.2 mmol) of (3aα,4β,7β,7aα)-4-amino-7-methyl-1,3,3a,4,7,7a-hexahydroisoindole in a mixture of 3 ml of dimethylformamide and 3 ml of acetonitrile under nitrogen at 80° C. for four hours. After the mixture has cooled, ice-water is added and the precipitate is isolated and stirred up with acetonitrile.

Yield: 310 mg (73% of theory)

Melting point: 212°–214° C. (with decomposition)

EXAMPLE 38

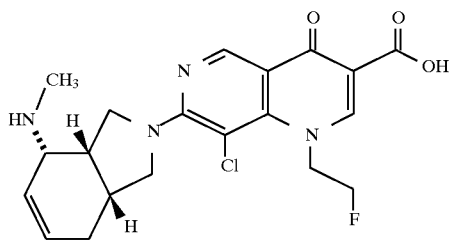

8-Chloro-1-(2-fluoroethyl)-1,4-dihydro-7-[(3aα,4β,
7aα)-4-methylamino-1,3,3a,4,7,7a-
hexahydroisoindol-2-yl]-4-oxo-1,6-naphthyridine-3-
carboxylic acid 305 mg (1 mmol) of 7,8-dichloro-1-(2-fluoroethyl)-1,4-dihydro-4-oxo-1,6-naphthyridine-3-carboxylic acid are stirred with 330 mg (2.2 mmol) of (3aα,4β,7aα)-4-methylamino-1,3,3a,4,7,7a-hexahydroisoindole in a mixture of 3 ml of dimethylformamide and 3 ml of acetonitrile under nitrogen at 80° C. for four hours. After the mixture has cooled, ice-water is added and the precipitate is isolated and stirred up with acetonitrile.

Yield: 340 mg (80% of theory)

Melting point: 220°–221° C. (with decomposition)

EXAMPLE 39

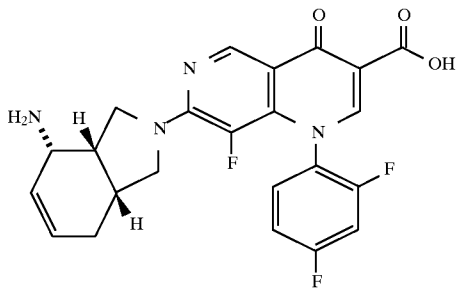

7-[(3aα,4β,7aα)-4-Amino-1,3,3a,4,7,7a-
hexahydroisoindol-2-yl]-8-fluoro-1-(2,4-
difluorophenyl)-1,4-dihydro-4-oxo-1,6-
naphthyridine-3-carboxylic acid 354 mg (1 mmol) of 7-chloro-8-fluoro-1-(2,4-difluorophenyl)-1,4-dihydro-4-oxo-1,6-naphthyridine-3-carboxylic acid are stirred with 303 mg (2.2 mmol) of (3aα,4β,7aα)-4-amino-1,3,3a,4,7,7a-hexahydroisoindole in a mixture of 3 ml of dimethylformamide and 3 ml of acetonitrile under nitrogen at 80° C. for four hours. After the mixture has cooled, ice-water is added and the precipitate is isolated and stirred up with acetonitrile.

Yield: 380 mg (83% of theory)

Melting point: 261°–263° C. (with decomposition)

EXAMPLE 40

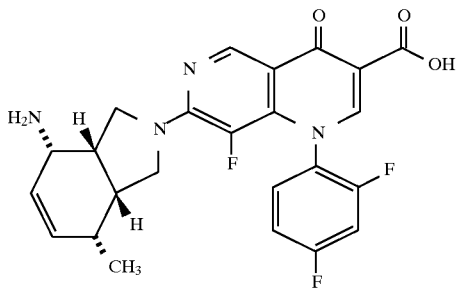

7-[(3aα,4β,7β,7aα)-4-Amino-7-methyl-1,3,3a,4,7,
7a-hexahydroisoindol-2-yl]-8-fluoro-1-(2,4
-difluorophenyl)-1,4-dihydro-4-oxo-1,6-
naphthyridine-3-carboxylic acid 354 mg (1 mmol) of 7-chloro-8-fluoro-1-(2,4-difluorophenyl)-1,4-dihydro-4-oxo-1,6-naphthyridine-3-carboxylic acid are stirred with 330 mg (2.2 mmol) of (3aα,4β,7β,7aα)-4-amino-7-methyl-1,3,3a,4,7,7a-hexahydroisoindole in a mixture of 3 ml of dimethylformamide and 3 ml of acetonitrile under nitrogen at 80° C. for four hours. After the mixture has cooled, ice-water is added and the precipitate is isolated and stirred up with acetonitrile.

Yield: 410 mg (87% of theory)

Melting point: 158°–162° C. (with decomposition)

EXAMPLE 41

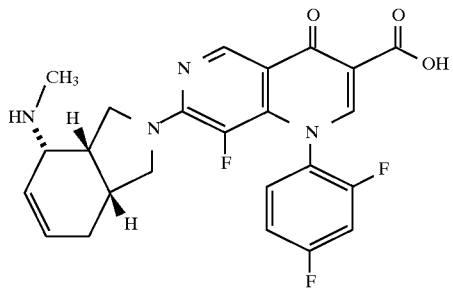

8-Fluoro-1-(2,4-difluorophenyl)-1,4-dihydro-7-[(3aα,4β,7aα)-4-methylamino-1,3,3a,4,7,7a-hexahydroisoindol-2-yl]-4-oxo-1,6-naphthyridine-3-carboxylic acid 177 mg (0.5 mmol) of 7-chloro-8-fluoro-1-(2,4-difluorophenyl)-1,4-dihydro-4-oxo-1,6-naphthyridine-3-carboxylic acid are stirred with 167 mg (1.1 mmol) of (3aα,4β,7aα)-4-methylamino-1,3,3a,4,7,7a-hexahydroisoindole in a mixture of 1.5 ml of dimethylformamide and 1.5 ml of acetonitrile under nitrogen at 80° C. for four hours. After the mixture has cooled, ice-water is added and the precipitate is isolated and stirred up with acetonitrile.

Yield: 170 mg (72% of theory)

Melting point: 209°–210° C. (with decomposition)

EXAMPLE 42

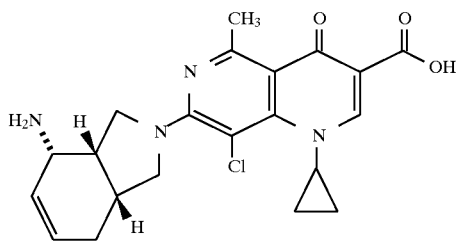

7-[(3aα,4β,7aα)-4-Amino-1,3,3a,4,7,7a-hexahydroisoindol-2-yl]-8-chloro-1-cyclopropyl-1,4-dihydro-5-methyl-4-oxo-1,6-naphthyridine-3-carboxylic acid 313 mg (1 mmol) of 7,8-dichloro-1-cyclopropyl-1,4-dihydro-5-methyl-4-oxo-1,6-naphthyridine-3-carboxylic acid are stirred with 303 mg (2.2 mmol) of (3aα,4β,7aα)-4-amino-1,3,3a,4,7,7a-hexahydroisoindole in a mixture of 3 ml of dimethylformamide and 3 ml of acetonitrile under nitrogen at 80° C. for four hours. After the mixture has cooled, ice-water is added and the precipitate is isolated and stirred up with acetonitrile.

Yield: 320 mg (77% of theory)

Melting point: 225°–227° C. (with decomposition)

EXAMPLE 43

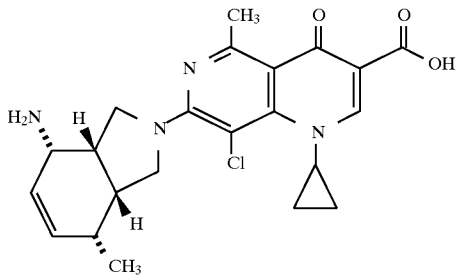

7-[(3aα,4β,7β,7aα)-4-Amino-7-methyl-1,3,3a,4,7,7a-hexahydroisoindol-2-yl]-8-chloro-1-cyclopropyl-1,4-dihydro-5-methyl-4-oxo-1,6-naphthyridine-3-carboxylic acid 312 mg (1 mmol) of 7,8-dichloro-1-cyclopropyl-1,4-dihydro-5-methyl-4-oxo-1,6-naphthyridine-3-carboxylic acid are stirred with 330 mg (2.2 mmol) of (3aα,4β,7β,7aα)-4-amino-7-methyl-1,3,3a,4,7,7a-hexahydroisoindole in a mixture of 3 ml of dimethylformamide and 3 ml of acetonitrile under nitrogen at 80° C. for four hours. After the mixture has cooled, ice-water is added and the precipitate is isolated and stirred up with acetonitrile.

Yield: 320 mg (74% of theory)

Melting point: 164°–166° C. (with decomposition)

EXAMPLE 44

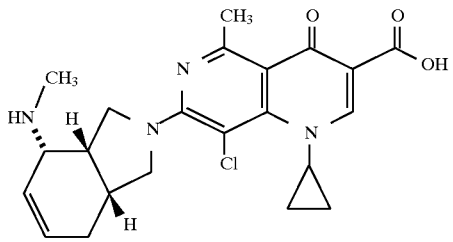

8-Chloro-1-cyclopropyl-1,4-dihydro-5-methyl-7-[(3aα,4β,7aα)-4-methylamino-1,3,3a,4,7,7a-hexahydroisoindol-2-yl]-4-oxo-1,6-naphthyridine-3-carboxylic acid 313 mg (1 mmol) of 7,8-dichloro-1-cyclopropyl-1,4-dihydro-4-oxo-1,6-naphthyridine-3-carboxylic acid are stirred with 330 mg (22 mmol) of (3aα,4β,7aα)-4-methylamino-1,3,3a,4,7,7a-hexahydroisoindole in a mixture of 3 ml of dimethylformamide and 3 ml of acetonitrile under nitrogen at room temperature overnight. Subsequently, ice-water is added and the precipitate is isolated and stirred up with acetonitrile.

Yield: 340 mg (79% of theory)

Melting point: 165°–167° C. (with decomposition)

EXAMPLE 45

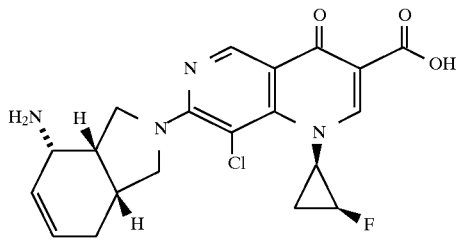

7-[(3aα,4β,7aα)-4-Amino-1,3,3a,4,7,7a-hexahydroisoindol-2-yl]-8-chloro-1-[(1R,2S)-2-fluorocyclopropyl-1,4-dihydro-4-oxo-1,6-naphthyridine-3-carboxylic acid 238 mg (0.75 mmol) of 7,8-dichloro-1-[(1R,2S)-2-fluorocyclopropyl-1,4-dihydro-4-oxo-1,6-naphthyridine-3-carboxylic acid are stirred with 230 mg (1.65 mmol) of (3aα,4β,7aα)-4-amino-1,3,3a,4,7,7a-hexahydroisoindole in a mixture of 2.2 ml of dimethylformamide and 2.2 ml of acetonitrile under nitrogen at room temperature overnight. Subsequently, ice-water is added and the precipitate is isolated and stirred up with acetonitrile.

Yield: 230 mg (71% of theory)

Melting point: 224°–226° C. (with decomposition)

EXAMPLE 46

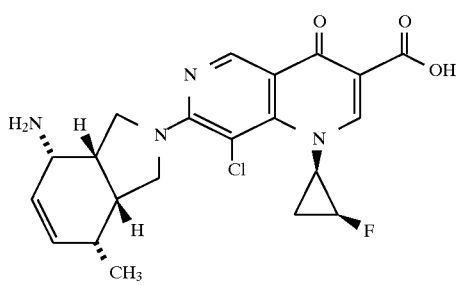

7-[(3aα,4β,7aα)-4-Amino-7-methyl-1,3,3a,4,7,7a-hexahydroisoindol-2-yl]-8-chloro-1-[(1R,2S)-2-fluorocyclopropyl-1,4-dihydro-5-methyl-4-oxo-1,6-naphthyridine-3-carboxylic acid 238 mg (0.75 mmol) of 7,8-dichloro-1-[(1R,2S)-2-fluorocyclopropyl-1,4-dihydro-4-oxo-1,6-naphthyridine-3-carboxylic acid are stirred with 250 mg (1.65 mmol) of (3aα,4β,7β,7aα)-4-amino-7-methyl-1,3,3a,4,7,7a-hexahydro-isoindole in a mixture of 2.2 ml of dimethylformamide and 2.2 ml of acetonitrile under nitrogen at 60° C. for three hours. The solvents are removed in vacuo, ice-water is added and the precipitate is isolated and stirred up with acetonitrile.

Yield: 190 mg (59% of theory)

Melting point: 208°–210° C. (with decomposition)

EXAMPLE 47

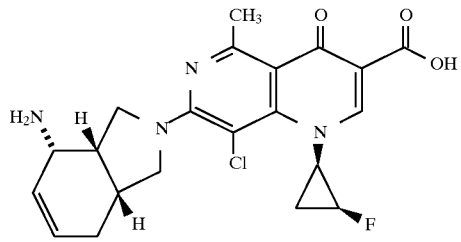

7-[(3aα,4β,7aα)-4-Amino-1,3,3a,4,7,7a-hexahydroisoindol-2-yl]-8-chloro-1-[(1R,2S)-2-fluorocyclopropyl-1,4-dihydro-5-methyl-4-oxo-1,6-naphthyridine-3-carboxylic acid 248 mg (0.75 mmol) of 7,8-dichloro-1-[(1R,2S)-2-fluorocyclopropyl-1,4-dihydro-5-methyl-4-oxo-1,6-naphthyridine-3-carboxylic acid are stirred with 230 mg (1.65 mmol) of (3aα,4β,7aα)-4-amino-1,3,3a,4,7,7a-hexahydroisoindole in a mixture of 2.2 ml of dimethylformamide and 2.2 ml of acetonitrile under nitrogen at 60° C. for four hours. The solvents are removed in vacuo, ice-water is added to the residue, and the precipitate is isolated and stirred up with acetonitrile.

Yield: 210 mg (65% of theory)

Melting point: 164°–166° C. (with decomposition)

EXAMPLE 48

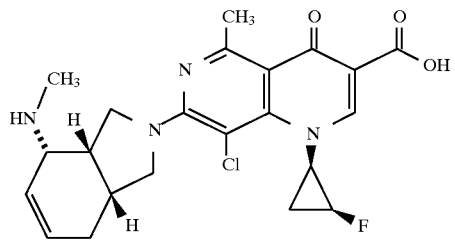

8-Chloro-1-[(1R,2S)-2-fluorocyclopropyl-1,4-dihydro-5-methyl-7-[(3aα,4β,7aα)-4-methylamino-1,3,3a,4,7,7a-hexahydroisoindol-2-yl]-4-oxo-1,6-naphthyridine-3-carboxylic acid 496 mg (1.5 mmol) of 7,8-dichloro-1-[(1R-2S)-2-fluorocyclopropyl-1,4-dihydro-5-methyl-4-oxo-1,6-naphthyridine-3-carboxylic acid are stirred with 500 mg (3.3 mmol) of (3aα,4β,7aα)4-methylamino-1,3,3a,4,7,7a-hexahydroisoindole in a mixture of 4.4 ml of dimethylformamide and 4.4 ml of acetonitrile under nitrogen at room temperature for two days. The solvents are removed in vacuo, ice-water is added, the pH is adjusted to 7 with dilute hydrochloric acid and the precipitate is isolated and stirred up with acetonitrile.

Yield: 550 mg (82% of theory)

Melting point: 150°–152° C. (with decomposition)

EXAMPLE 49

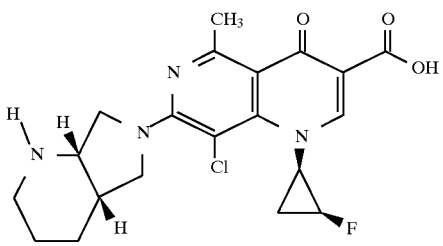

8-Chloro-1-[(1R,2S)-2-fluorocyclopropyl-1,4-dihydro-7-[(1S,6S)-2,8-diazabicyclo[4.3.0]nonan-8-yl]-5-methyl-4-oxo-1,6-naphthyridine-3-carboxylic acid 496 mg (1.5 mmol) of 7,8-dichloro-1-[(1R,2S)-2-fluorocyclopropyl-1,4-dihydro-5-methyl-4-oxo-1,6-naphthyridine-3-carboxylic acid are stirred with 420 mg (1.5 mmol) of (1S,6S)-2,8-diazabicyclo[4.3.0]nonane in a mixture of 4.4 ml of dimethylformamide and 4.4 ml of acetonitrile under argon at room temperature for two days. The solvents are removed in vacuo, water is added to the residue, the pH is adjusted to 7 with dilute hydrochloric acid, the precipitate is extracted with dichloromethane, and the extract is dried over sodium sulphate and concentrated on a rotary evaporator.

Yield: 550 mg (87% of theory)

Melting point: 147°–149° C. (with decomposition)

EXAMPLE 50

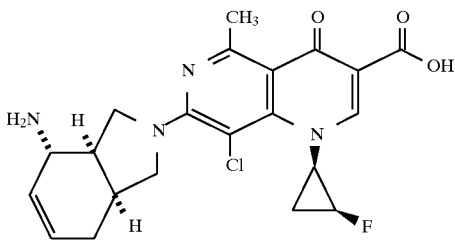

-[(3aα,4β,7aα)-4-Amino-1,3,3a,4,7,7a-hexahydroisoindol-2-yl]-8-chloro-1-[(1R,2S)-2-fluorocyclopropyl-1,4-dihydro-5-methyl-4-oxo-1,6-naphthyridine-3-carboxylic acid 248 mg (0.75 mmol) of 7,8-dichloro-1-[(1R,2S)-2-fluorocyclopropyl-1,4-dihydro-5-methyl-4-oxo-1,6-naphthyridine-3-carboxylic acid are stirred with 230 mg (1.65 mmol) of (3aα,4β,7aα)-4-amino-1,3,3a,4,7,7a-hexahydroisoindole in a mixture of 2.2 ml of dimethylformamide and 2.2 ml of acetonitrile under nitrogen at 60° C. for two hours. The solvents are removed in vacuo, ice-water is added, the pH is adjusted to 7 with dilute hydrochloric acid, and the precipitate is isolated and stirred up with acetonitrile.

Yield: 298 mg (90% of theory)

Melting point: 179°–180° C. (with decomposition)

We claim:
1. Compounds of the general formula (I)

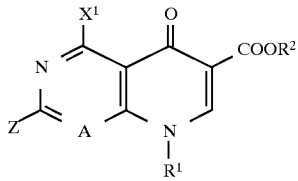

in which $R^1$ represents straight-chain or branched $C_1$–$C_4$-alkyl which is optionally substituted by hydroxyl, halogen or $C_1$–$C_3$-alkoxy, or represents $C_3$–$C_6$-cycloalkyl which is optionally substituted by $C_1$–$C_3$-alkyl or halogen, or represents $C_2$–$C_4$-alkenyl, $C_1$–$C_3$-alkoxy, amino, monoalkylamino having 1 to 3 carbon atoms, dialkylamino having 1 to 3 carbon atoms per alkyl group, or represents phenyl which is optionally substituted from one to three times by halogen, $R^2$ represents hydrogen, alkyl having 1 to 4 carbon atoms which is optionally substituted by hydroxyl, methoxy, amino, methylamino or dimethylamino, or represents (5-methyl-2-oxo-1,3-dioxol-4-yl)-methyl, $X^1$ represents hydrogen, halogen, amino, methyl or trifluoromethyl, Z represents radicals of the structures

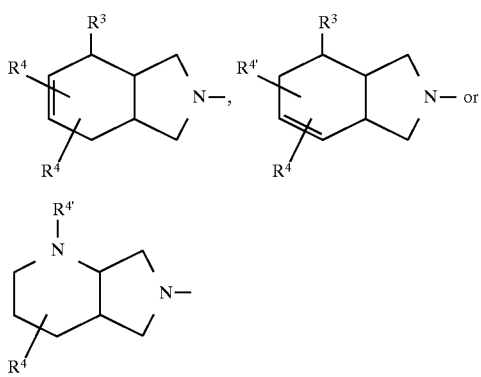

in which $R^3$ represents hydrogen, hydroxyl, —$NR^5R^6$, hydroxymethyl or —$CH_2$—$NR^5R^6$, where $R^5$ denotes hydrogen, $C_1$–$C_3$-alkyl which is optionally substituted by hydroxyl, or denotes alkoxycarbonyl having 1 to 4 carbon atoms in the alkoxy moiety or denotes $C_1$–$C_3$-acyl, and $R^6$ denotes hydrogen or methyl, $R^4$ represents hydrogen, straight-chain or branched $C_1$–$C_3$-alkyl or cyclopropyl, $R^{4'}$ represents hydrogen or methyl, A represents C—$R^7$, in which $R^7$ represents hydrogen, halogen, methyl, trifluoromethyl, vinyl, ethinyl, hydroxyl or methoxy or else, together with $R^1$, can form a bridge of the structure

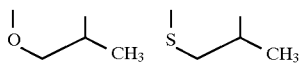

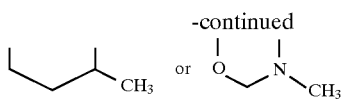

in the form of racemates or as enantiomerically pure compounds, pharmaceutically utilizable hydrates and acid addition salts thereof, and the alkali metal, alkaline earth metal, silver and guanidinium salts of the naphthyridonecarboxylic acids on which they are based.

2. Compounds according to claim 1, formula (I), in which
  $R^1$ represents $C_1$–$C_2$-alkyl which is optionally substituted by hydroxyl or fluorine, or represents $C_3$–$C_5$-cycloalkyl which is optionally substituted by fluorine, or represents vinyl, amino, monoalkylamino having 1 to 2 carbon atoms, dialkylamino having 1 to 2 carbon atoms per alkyl group, or represents phenyl which is optionally substituted from one to two times by halogen,
  $R^2$ represents hydrogen, alkyl having 1 to 2 carbon atoms which is optionally substituted by amino or dimethylamino, or represents (5-methyl-2-oxo-1,3-dioxol-4-yl)-methyl,
  $X^1$ represents hydrogen, fluorine, chlorine, amino, methyl or trifluoromethyl,
  Z represents radicals of the structures

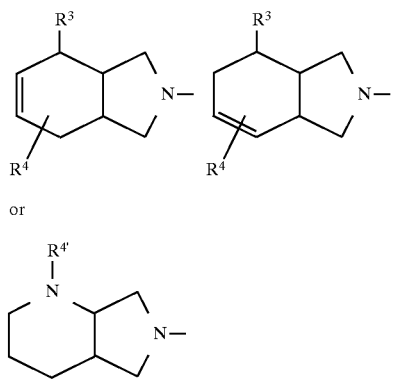

in which
  $R^3$ represents hydrogen, hydroxyl, —$NR^5R^6$, hydroxymethyl or —$CH_2$—$NR^5R^6$,
    where
      $R^5$ denotes hydrogen, $C_1$–$C_2$-alkyl which is optionally substituted by hydroxyl, or denotes alkoxycarbonyl having 1 to 4 carbon atoms in the alkoxy moiety, or denotes $C_1$–$C_3$-acyl, and
      $R^6$ denotes hydrogen or methyl,
  $R^4$ represents hydrogen, straight-chain or branched $C_1$–$C_3$-alkyl or cyclopropyl,
  $R^{4'}$ represents hydrogen or methyl,
  A represents C—$R^7$, in which
    $R^7$ represents hydrogen, chlorine, fluorine, methyl, trifluoromethyl, hydroxyl or methoxy, or else, together with $R^1$, can form a bridge of the structure

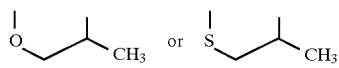

and the pharmaceutically utilizable hydrates and acid addition salts thereof, and also the alkali metal, alkaline earth metal, silver and guanidinium salts of the naphthyridonecarboxylic acids on which they are based.

3. Compounds according to claim 1, formula (I), in which
  $R^1$ represents methyl, ethyl, cyclopropyl which is optionally substituted by fluorine, or represents phenyl which is optionally substituted from one to two times by fluorine,
  $R^2$ represents hydrogen, methyl or ethyl,
  $X^1$ represents hydrogen, methyl or trifluoromethyl,
  Z represents radicals of the structures

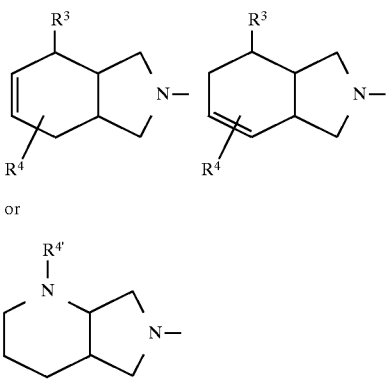

in which
  $R^3$ represents hydrogen, hydroxyl, —$NR^5R^6$, hydroxymethyl or —$CH_2$—$NR^5R^6$,
    where
      $R^5$ denotes hydrogen, methyl, alkoxycarbonyl having 1 to 4 carbon atoms in the alkoxy moiety, or denotes $C_1$–$C_3$-acyl, and
      $R^6$ denotes hydrogen or methyl,
  $R^4$ represents hydrogen, straight-chain or branched $C_1$–$C_3$-alkyl or cyclopropyl,
  $R^{4'}$ represents hydrogen or methyl,
  A represents C—$R^7$ in which
    $R^7$ represents hydrogen, chlorine, fluorine or methoxy, or else, together with $R^1$, can form a bridge of the structure

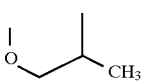

and the pharmaceutically utilizable hydrates and acid addition salts thereof, and also the alkali metal, alkaline earth metal, silver and guanidinium salts of the naphthyridonecarboxylic acid on which they are based.

4. Compounds according to claim 1 from the group consisting of
  7-[(3aα,4β,7β,7aα)-4-Amino-7-methyl-1,3,3 a,4,7,7a-hexahydroisoindol-2-yl]-8-chloro-1-cyclopropyl-1,4-dihydro-4-oxo-1,6-naphthyridine-3-carboxylic acid,
  7-[(3aα,4β,7aα)-4-Amino-1,3,3 a,4,7,7a-hexahydroisoindol-2-yl]-1-cyclopropyl-8-fluoro-1,4-dihydro-4-oxo-1,6-naphthyridine-3-carboxylic acid,
  7-[(3aα,4β,7β,7aα)-4-Amino-7-methyl-1,3,3a,4,7,7a-hexahydroisoindol-2-yl]-8-chloro-1-cyclopropyl-1,4-dihydro-5-methyl-4-oxo-1,6-naphthyridine-3-carboxylic acid,
  8-Chloro-1-cyclopropyl-1,4-dihydro-5-methyl-7-[(3aα,4β,7aα)-4-methylamino-1,3,3a,4,7,7a-hexahydroisoindol-2-yl]-4-oxo-1,6-naphthyridine-3-carboxylic acid,
  8-Chloro-1-[(1R,2S)-2-fluorocyclopropyl-1,4-dihydro-5-methyl-7-[(3aα,4β,7aα)-4-methylamino-1,3,3a,4,7,7a- hexahydroisoindol-2-yl]-4-oxo-1,6-naphthyridine-3-carboxylic acid and

8-Chloro-1-[(1R,2S)-2-fluorocyclopropyl-1,4-dihydro-7-[(1S,6S)-2,8-diazabicyclo[4.3.0]nonan-8-yl]-4-oxo-1,6-naphthyridine-3-carboxylic acid.

5. A compound according to claim 1, wherein such compound is 8-chloro-1-cyclopropyl-1,4-dihydro-5-methyl-7-[(3aα,4β,7aα)-4-methylamino-1,3,3a,4,7,7a-hexahydroisoindol-2-yl]-4-oxo-1,6-naphthyridine-3-carboxylic acid of the formula:

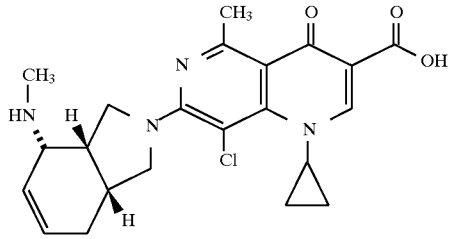

and its pharmaceutically utilizable hydrates and acid addition salts and the alkali metal, alkaline earth metal, silver and guanidinium salts.

6. Medicaments containing compounds according to claim 1.

7. Antimicrobial compositions containing compounds according to claims 1.

8. A pharmaceutical composition comprising a pharmaceutically effective amount of a compound or addition product thereof according to claim 1 and a diluent.

9. A composition according to claim 7 in the form of a tablet, capsule or ampule.

10. A method of combating bacteria in a patient in need thereof which comprises administering to such patient an antibacterially effective amount of a compound or addition product thereof according to claim 1.

* * * * *

UNITED STATES PATENT AND TRADEMARK OFFICE
CERTIFICATE OF CORRECTION

PATENT NO : 5,811,433
DATED : September 22, 1998
INVENTOR(S): Stephan Bartel

It is certified that error appears in the above-identified patent and that said Letters Patent is hereby corrected as shown below:

Col. 44, Claim 1, Line 32  After "Z represents radicals of the structures" delete " 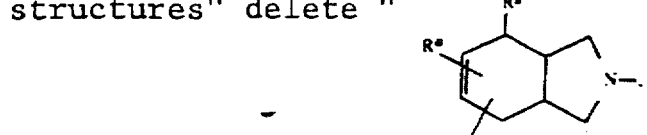 "

and insert 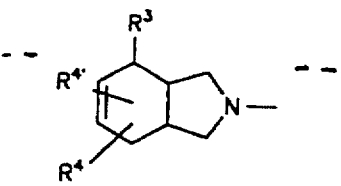

Signed and Sealed this

Fifteenth Day of February, 2000

Attest:

Q. TODD DICKINSON

Attesting Officer    Commissioner of Patents and Trademarks